US010222321B2

(12) United States Patent
Yamamoto et al.

(10) Patent No.: US 10,222,321 B2
(45) Date of Patent: Mar. 5, 2019

(54) LAMINATE SUBSTRATE MEASUREMENT METHOD, LAMINATE SUBSTRATE AND MEASUREMENT APPARATUS

(71) Applicant: SUMITOMO CHEMICAL COMPANY, LIMITED, Tokyo (JP)

(72) Inventors: Taiki Yamamoto, Tsukuba (JP); Taketsugu Yamamoto, Tsukuba (JP); Kenji Kasahara, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/718,198

(22) Filed: Sep. 28, 2017

(65) Prior Publication Data

US 2018/0017484 A1   Jan. 18, 2018

Related U.S. Application Data

(63) Continuation of application No. PCT/JP2016/059699, filed on Mar. 25, 2016.

(30) Foreign Application Priority Data

Mar. 29, 2015 (JP) ................. 2015-067788
Mar. 29, 2015 (JP) ................. 2015-067789

(51) Int. Cl.
*G01N 21/21* (2006.01)
*G01B 11/06* (2006.01)
*G01N 21/33* (2006.01)

(52) U.S. Cl.
CPC ............. *G01N 21/21* (2013.01); *G01B 11/06* (2013.01); *G01B 11/0633* (2013.01);
(Continued)

(58) Field of Classification Search
CPC . G01B 11/06; G01B 11/0633; G01B 11/0641; G01N 2021/213; G01N 21/21; G01N 21/211; G01N 2201/12
See application file for complete search history.

(56) References Cited

U.S. PATENT DOCUMENTS

| | | | |
|---|---|---|---|
| 6,392,756 B1 | 5/2002 | Li et al. | |
| 2006/0068513 A1 | 3/2006 | Funakubo et al. | |
| 2006/0281201 A1* | 12/2006 | Hachigo | G01N 21/211 438/16 |
| 2013/0256686 A1 | 10/2013 | Kanamura | |
| 2014/0042451 A1 | 2/2014 | Sugiyama et al. | |
| 2014/0175455 A1 | 6/2014 | Tanimoto | |

FOREIGN PATENT DOCUMENTS

| | | |
|---|---|---|
| JP | 2002-340528 A | 11/2002 |
| JP | 2003-315257 A | 11/2003 |

(Continued)

OTHER PUBLICATIONS

International Preliminary Report on Patentability and English translation of the Written Opinion of the International Searching Authority (Forms PCT/IB/326, PCT/IB/373 and PCT/ISA/237), dated Oct. 12, 2017, for International Application No. PCT/JP2016/059699.

(Continued)

*Primary Examiner* — David P Porta
*Assistant Examiner* — Faye Boosalis
(74) *Attorney, Agent, or Firm* — Birch, Stewart, Kolasch & Birch, LLP

(57) ABSTRACT

A measurement method for a laminate substrate is provided. The laminate substrate has: a base substrate; an absorption layer; and a measurement-target layer in this order. The measurement-target layer has a single measurement-target monolayer or a plurality of measurement-target monolayers. The method includes: emitting incident light including light with a wavelength shorter than a threshold wavelength from (Continued)

a side on which the measurement-target layer is positioned, and measuring reflected light and acquiring mutually independent 2n (n is a layer count of the measurement-target monolayers included in the measurement-target layer and is an integer equal to one or larger) or more reflected light-related values for wavelengths equal to the threshold wavelength or shorter; and calculating values related to the measurement-target monolayers for each measurement-target monolayer included in the measurement-target layer using the 2n or more reflected light-related values.

48 Claims, 28 Drawing Sheets

(52) U.S. Cl.
CPC ........ *G01B 11/0641* (2013.01); *G01N 21/211* (2013.01); *G01N 21/33* (2013.01); *G01N 2021/213* (2013.01); *G01N 2201/12* (2013.01)

(56) References Cited

FOREIGN PATENT DOCUMENTS

| | | |
|---|---|---|
| JP | 2006-349374 A | 12/2006 |
| JP | 2013-207274 A | 10/2013 |
| JP | 2014-90033 A | 5/2014 |
| JP | 2014-110311 A | 6/2014 |
| JP | 2014-140024 A | 7/2014 |
| JP | 2014-236017 A | 12/2014 |
| WO | WO 2014/024310 A1 | 2/2014 |

OTHER PUBLICATIONS

International Search Report, issued in PCT/JP2016/059699, dated Jun. 14, 2016.
Extended European Search report dated Sep. 28, 2018 for Application No. 16772666.0.

* cited by examiner

LAMINATE SUBSTRATE MEASUREMENT METHOD, LAMINATE SUBSTRATE AND MEASUREMENT APPARATUS

CROSS REFERENCE TO RELATED APPLICATIONS

This application is a Continuation of PCT International Application No. PCT/JP2016/059699, filed on Mar. 25, 2016, which claims priority under 35 U.S.C. 119(a) to Patent Application Nos. 2015-067788 and 2015-067789, each filed in Japan on Mar. 29, 2015, all of which are hereby expressly incorporated by reference into the present application.

BACKGROUND

1. Technical Field

The present invention relates to a laminate substrate measurement method, laminate substrate and measurement apparatus.

2. Related Art

As methods of measuring the composition or thickness of a thin film formed on a substrate, there are X-ray diffraction analysis, X-ray reflection methods, PL (photoluminescence) methods, cross-section observation methods using TEMs (transmission electron microscopes), spectroscopic ellipsometry or the like.

As a method of measuring the thickness or composition of a thin film using spectroscopic ellipsometry, for example, Patent Document 1 discloses "THIN FILM MEASUREMENT METHOD USING SPECTROSCOPIC ELLIPSOMETER" for the purpose of determining thin film structures and wavelength dependence of dielectric constants with good precision and accuracy. The thin film measurement method is explained as follows: In Steps 10, 20 of generating $\Psi_E$, $\Delta_E$ spectrum measurement data, measurement spectrums $\Psi_E(\lambda_i)$ and $\lambda_E(\lambda_i)$ which indicate changes in polarization of incident light and reflected light, for each wavelength $\lambda_i$, observed when the wavelength of incident light is changed about a thin film of a measurement-target substrate surface are obtained. In Steps 21, 22 of calculating $\Psi_{Mk}$, $\Delta_{Mk}$ modelling spectrums, ($N_0$ ($n_0$, $k_0$)) of the substrate, ($d_1$, $N_1$ ($n_1$, $k_1$)) of a first layer, and ($d_j$, $N_j$ ($n_j$, $k_j$)) of a j-th layer are hypothesized using a dispersion formula, and furthermore a plurality of models using $\phi_k$ around the nominal angle of incidence ($\phi_0$) as a function are established, and from them, the modelling spectrums $\Psi_{Mk}(\lambda_i)$ and $\Delta_{Mk}(\lambda_i)$ are obtained. In Steps 23, 24 of comparison and evaluation, the $\Psi_E$, $\Delta_E$ spectrums and the $\Psi_{Mk}$, $\Delta_{Mk}$ modelling spectrums are compared, and structures that meet an evaluation reference are determined as measurement results.

For example, Patent Document 2 discloses "METHOD OF DETERMINING COMPOSITION OF POLYCRYSTALLINE COMPOUND SEMICONDUCTOR USING SPECTROSCOPIC ELLIPSOMETER" for the purpose of calculating the composition of a polycrystalline compound semiconductor from data obtained using an ellipsometer. The composition determining method is explained as follows: In Step 10 of measuring a spectrum, a measurement spectrum that indicates changes in polarization of incident light and reflected light for each wavelength $\lambda_i$, observed when the wavelength of incident light is changed about the measurement-target polycrystalline compound semiconductor layer is obtained. In Steps 20, 30 of analysis, a plurality of types of model are obtained, and fitting with the measurement spectrum is performed for the composition ratio, mixing ratio, film thickness, dispersion formula and the like of the compound semiconductor for each model, and the best model is determined. In Step 40 of calculation, the concentration of atoms of interest of the polycrystalline compound semiconductor is calculated based on the mixing ratio of each crystalline compound semiconductor of the selected best model and the composition ratio of the atoms of interest in the crystalline compound semiconductor.

PRIOR ART DOCUMENTS

Patent Documents

[Patent Document 1] Japanese Patent Application Publication No. 2002-340528
[Patent Document 2] Japanese Patent Application Publication No. 2003-315257

The composition and thickness of a compound semiconductor layer greatly affect, for example, the concentration of a two-dimensional electron gas (2 DEG) at a heterointerface formed of the compound semiconductor layer. For this reason, from the perspective of properly managing the performance of a semiconductor device having the heterointerface as a channel, it is necessary to properly manage the composition and thickness of a compound semiconductor layer, and as a presumption of the management, it is desired to measure the composition and thickness of the compound semiconductor layer with accuracy and good efficiency. Taking into consideration the fact that the thickness of each layer of a compound semiconductor layer to constitute a heterointerface that generates a 2DEG is normally several dozens of nanometers, the precision of thickness measurement needs to be in the order of nanometer, and taking into consideration utilization at production processes, it is also desired that the measurement throughput be high and mapping measurement over the entire region in a wafer surface be possible.

In this respect, X-ray diffraction analysis, X-ray reflection methods and TEM cross-section observation methods provide low measurement throughput, and X-ray reflection methods and TEM cross-section observation method are also not suited to mapping measurement. Also, PL makes it possible to measure the composition of a compound semiconductor layer, but its thickness cannot be measured.

On the other hand, spectroscopic ellipsometry provides high measurement throughput, and enables mapping measurement, so is promising as an approach of measuring the composition and thickness of a compound semiconductor layer. However, under a measurement-target compound semiconductor layer, normally a number of layers are laminated, and if a superlattice buffer layer or the like is used, the number of laminated layers is often as many as dozens or more. In such a case, an analysis model in spectroscopic ellipsometry becomes complicated, and it is difficult to attain convergence in fitting in some cases.

An object of the present invention is to provide a technique that enables mapping measurement of the composition and thickness of a compound semiconductor layer with high precision and high throughput even if there is a complicated base layer configuration.

SUMMARY

Therefore, it is an object of an aspect of the innovations herein to provide a laminate substrate measurement method, which is capable of overcoming the above drawbacks accompanying the related art. The above and other objects can be achieved by combinations described in the claims. In other words, to solve the above-mentioned drawbacks, a first aspect of the present invention provides a laminate substrate measurement method for a laminate substrate having: a base substrate; a measurement-target layer; and an absorption layer positioned between the base substrate and the measurement-target layer, wherein the measurement-target layer includes: a measurement-target monolayer which is a monolayer or a measurement-target laminate layer formed by laminating a plurality of the measurement-target monolayers, the laminate substrate measurement method includes: emitting incident light including light with a wavelength shorter than a threshold wavelength toward a surface of the laminate substrate on a side on which the measurement-target layer is positioned, and measuring reflected light of the incident light from the laminate substrate and acquiring mutually independent 2n (n is a layer count of the measurement-target monolayers included in the measurement-target layer and is an integer equal to one or larger) or more reflected light-related values for wavelengths equal to the threshold wavelength or shorter; and calculating values related to the measurement-target monolayers for each measurement-target monolayer included in the measurement-target layer using the 2n or more reflected light-related values, and the threshold wavelength used is a maximum wavelength in a wavelength range over which an absolute value of a first-order derivative $dk(\lambda)/d\lambda$ obtained if an extinction coefficient k of the absorption layer is expressed as a function $k(\lambda)$ of a wavelength $\lambda$ (expressed in nm) becomes equal to an extinction derivative threshold value or lower.

A second aspect of the present invention provides a laminate substrate that is applicable to a laminate substrate measurement method, wherein the laminate substrate measurement method includes: emitting incident light including light with a wavelength shorter than a threshold wavelength toward a surface on a side on which a measurement-target layer including a measurement-target monolayer or a measurement-target laminate layer formed by laminating a plurality of the measurement-target monolayers is positioned, and measuring reflected light of the incident light and acquiring mutually independent two or more reflected light-related values for wavelengths equal to the threshold wavelength or shorter; and calculating values related to the measurement-target monolayers for each measurement-target monolayer included in the measurement-target layer using 2n (n is a layer count of the measurement-target monolayers included in the measurement-target layer and is an integer equal to one or larger) or more reflected light-related values, the laminate substrate includes a base substrate; the measurement-target layer; and an absorption layer positioned between the base substrate and the measurement-target layer, and the threshold wavelength used in the measurement method is a maximum wavelength in a wavelength range over which an absolute value of a first-order derivative $dk(\lambda)/d\lambda$ obtained if an extinction coefficient k of the absorption layer is expressed as a function $k(\lambda)$ of a wavelength $\lambda$ (expressed in nm) becomes equal to an extinction derivative threshold value or lower.

A third aspect of the present invention provides a measurement apparatus that is applicable to the measurement method, the measurement apparatus including: a substrate holding unit that holds the laminate substrate; a light source unit that generates the incident light; a reception-light signal generating unit that receives the reflected light and generates a reception-light signal; an angle control mechanism that controls angles of the substrate holding unit, the light source unit and the reception-light signal generating unit; and a signal processing unit that processes the reception-light signal generated at the reception-light signal generating unit.

DESCRIPTION OF EXEMPLARY EMBODIMENTS

Hereinafter, (some) embodiment(s) of the present invention will be described. The embodiments do not limit the invention according to the claims, and all the combinations of the features described in the embodiments are not necessarily essential to means provided by aspects of the invention.

Figure 1:
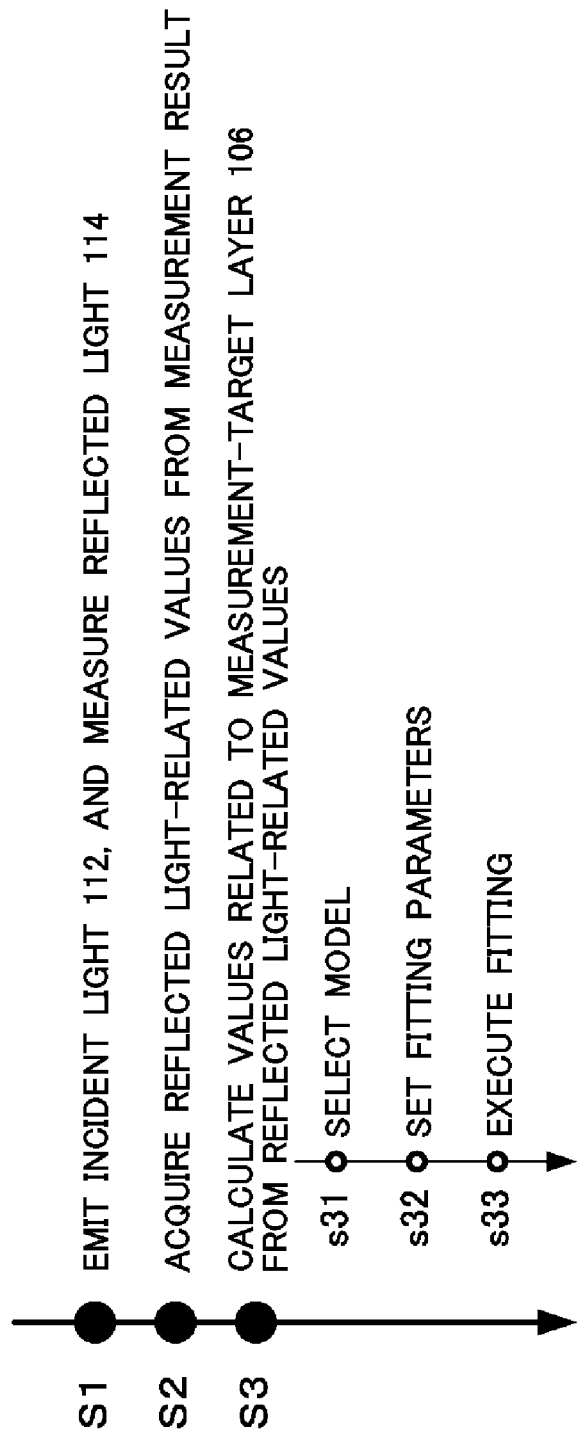
FIG. 1 is a flow chart showing the outline of a measurement method which is one embodiment of the present invention.
Figure 2:
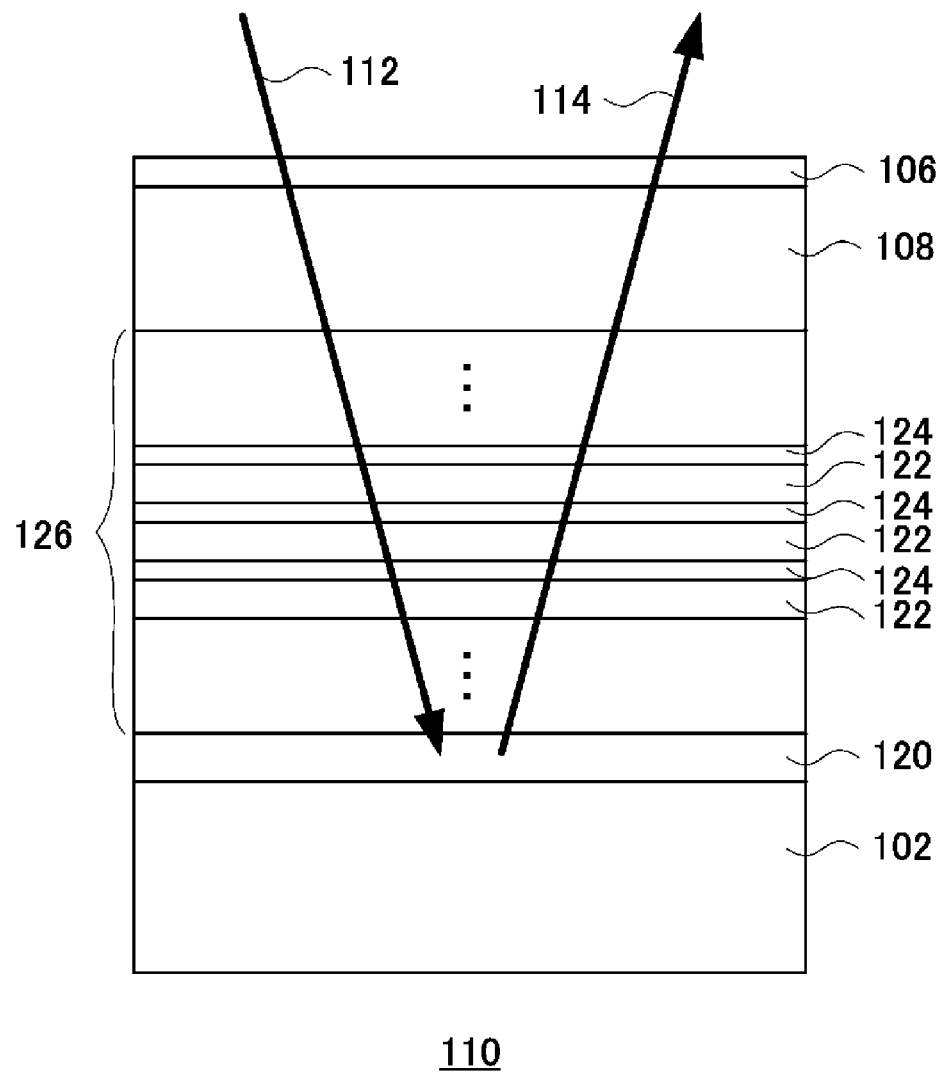
FIG. 2 is a cross sectional view of a measurement target laminate substrate 110.

FIG. 1 is a flow chart showing the outline of a measurement method according to the present embodiment, and FIG. 2 is a cross sectional view of a measurement target laminate substrate 110. A laminate substrate measurement method of the present embodiment includes emitting incident light 112 toward a surface of the laminate substrate 110, measuring reflected light 114 from the laminate substrate 110 and calculating a value related to a measurement-target layer 106.

The measurement target laminate substrate 110 has a base substrate 102, the measurement-target layer 106 and an absorption layer 108. The base substrate 102, the measurement-target layer 106 and the absorption layer 108 are arranged in the order of the base substrate 102, the absorption layer 108 and the measurement-target layer 106 as illustrated. An intermediate layer 120 and a buffer layer 126 are formed between the base substrate 102 and the absorption layer 108.

The base substrate 102 is a substrate supporting each layer above the intermediate layer 120 (which may be sometimes referred to as simply "each layer", hereinafter). The base substrate 102 can be any substrate as long as it has mechanical strength, chemical stability and thermal stability necessary for formation of each layer, and its shape, material quality and the like are not limited particularly. If each layer is a semiconductor crystal layer formed by epitaxial growth, a material suited to a crystal layer to be formed is selected for the base substrate 102. If each layer is a gallium nitride-based semiconductor crystal layer, the base substrate 102 may be a silicon substrate, sapphire substrate, GaN substrate, AlN substrate, SiC substrate or the like.

The base substrate 102 preferably is a wafer substrate having a diameter of 150 mm or larger. By using a wafer substrate having a diameter of 150 mm or larger, for example, a 6-inch wafer substrate or 8-inch wafer substrate, it becomes possible to utilize a conventional semiconductor manufacturing apparatus adapted for silicon wafers, and the manufacturing cost of the laminate substrate 110 can be lowered. Also, in the measurement method explained below, a substrate with a large area, such as a 6-inch substrate or 8-inch substrate, can be a measurement target.

The intermediate layer 120 and the buffer layer 126 are layers provided for mitigation, adjustment or the like of stress attributable to a difference in coefficients of thermal expansion between the base substrate 102 and the absorption layer 108. The buffer layer 126 may be a superlattice structure layer formed by laminating, alternately and repeatedly many times, first crystal layers 122 and second crystal layers 124 which have different compositions. Examples of the intermediate layer 120 may include a layer formed by laminating AlN layers and AlGaN layers for example. Examples of the buffer layer 126 may include a superlattice structure layer formed by laminating AlN layers and AlGaN layers alternately and repeatedly many times for example.

The absorption layer 108 is a layer having optical properties of absorbing short wavelength components in the incident light 112 and transmitting long wavelength components in the incident light 112. If the absorption layer 108 and the measurement-target layer 106 are constituted by compound semiconductor layers having different compositions such as a GaN layer and an AlGaN layer for example, a two-dimensional electron gas (2DEG) is generated at the heterointerface between the absorption layer 108 and the measurement-target layer 106. A high electron mobility transistor and the like can be formed using the 2DEG as carrier. Because in such a case, the composition and thickness of the measurement-target layer 106 greatly affect the carrier concentration of the 2DEG, it is meaningful to measure the composition and thickness of the measurement-target layer 106 with high precision and simplicity. The absorption layer 108 may be any of a monolayer and a laminate layer, and the layer configuration of the absorption layer 108, if it is a laminate layer, can have any configuration.

FIG. 3 to FIG. 6 are cross sectional views showing enlarged views of examples of a surface portion of the laminate substrate 110. Each figure among FIG. 3 to FIG. 6 shows a different configuration example of the measurement-target layer 106. The measurement-target layer 106 is a target of the measurement method of the present embodiment, and has a measurement-target laminate layer 104 formed by laminating a plurality of measurement-target monolayers or a measurement-target monolayer 105 which is a monolayer. In the following explanation, the layer count of measurement-target monolayers included in the measurement-target layer 106 is assumed to be "n". The measurement-target layer 106 includes n (where n is an integer equal to one or larger) measurement-target monolayers. The measurement-target monolayers are layers that can be optically regarded as a single layer, and need not necessarily have uniform compositions in the thickness direction. For example, variation in compositions in the thickness direction is tolerated to a degree that does not generate reflection or diffraction of light in the measurement-target monolayers. Optional intermediate layers may be formed between respective measurement-target monolayers included in the measurement-target layer 106, between the measurement-target layer 106 and the absorption layer 108, in layers of the measurement-target layer 106 and in a layer of the absorption layer 108. The intermediate layers may be any of semiconductor layers and insulating layers. The measurement-target layer 106 may have a laminate structure.

Figure 3:
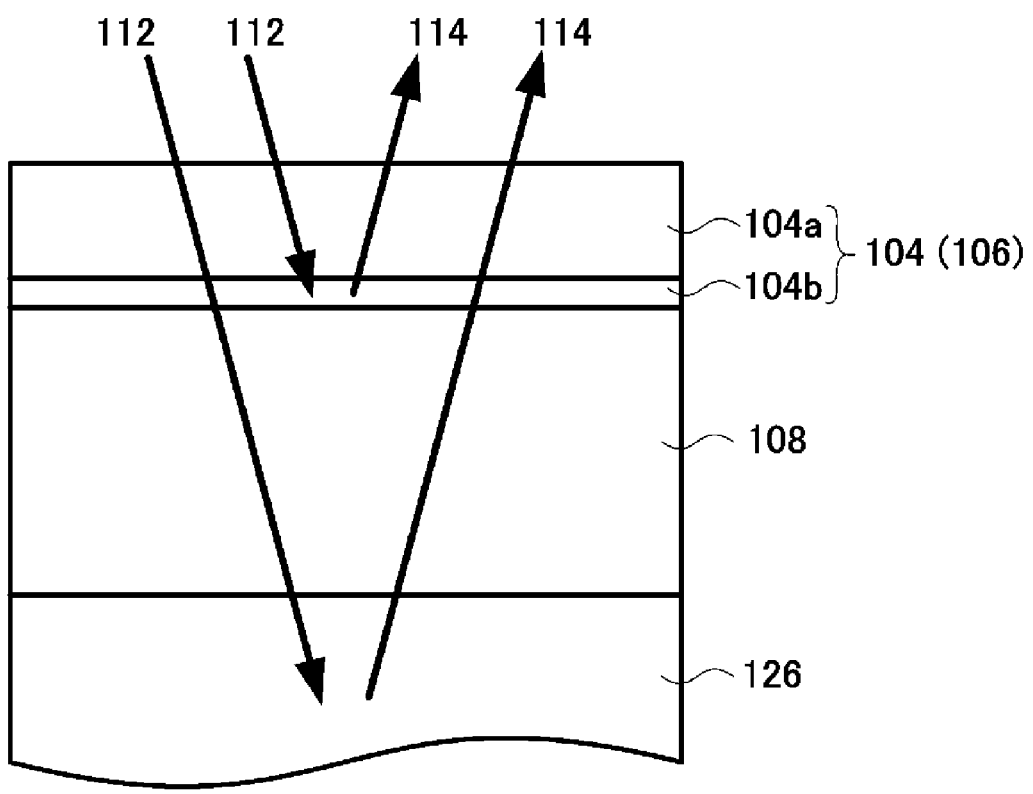
FIG. 3 is a cross sectional view showing an enlarged view of one example of a surface portion of the laminate substrate 110.
Figure 4:
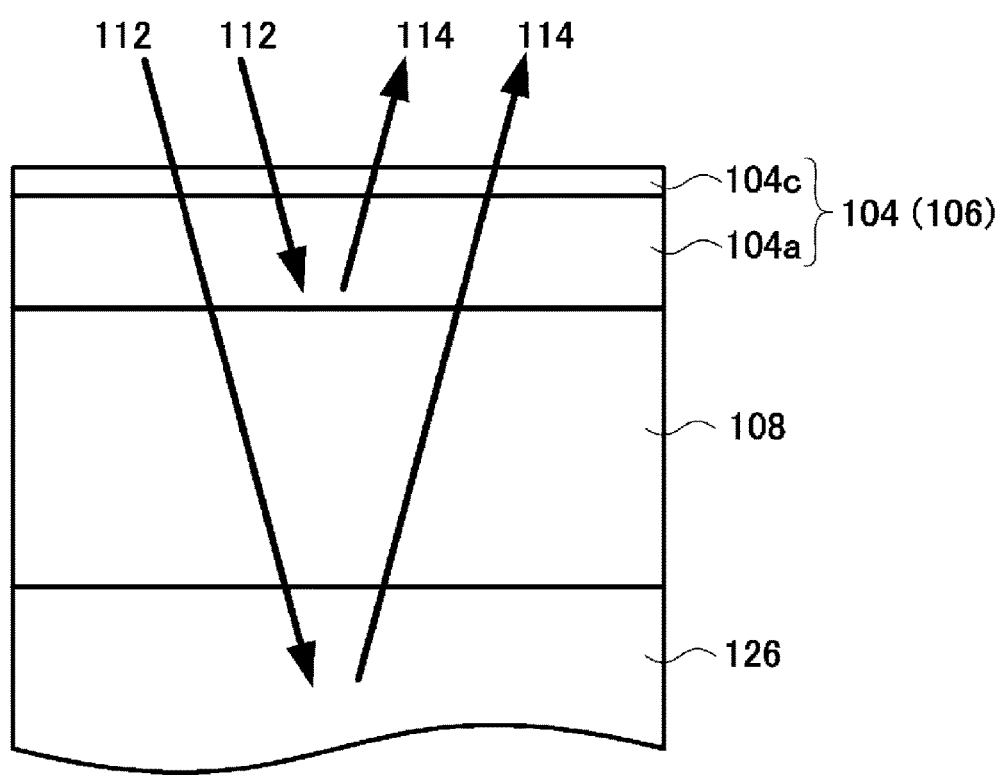
FIG. 4 is a cross sectional view showing an enlarged view of one example of a surface portion of the laminate substrate 110.
Figure 5:
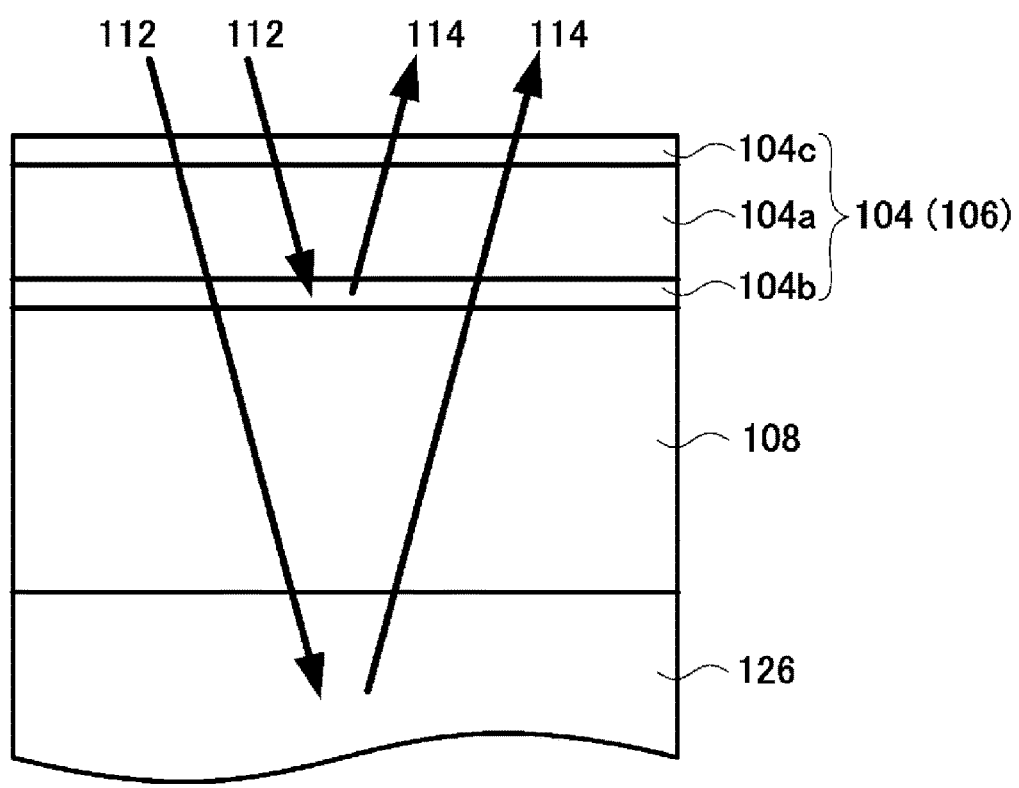
FIG. 5 is a cross sectional view showing an enlarged view of one example of a surface portion of the laminate substrate 110.
Figure 6:
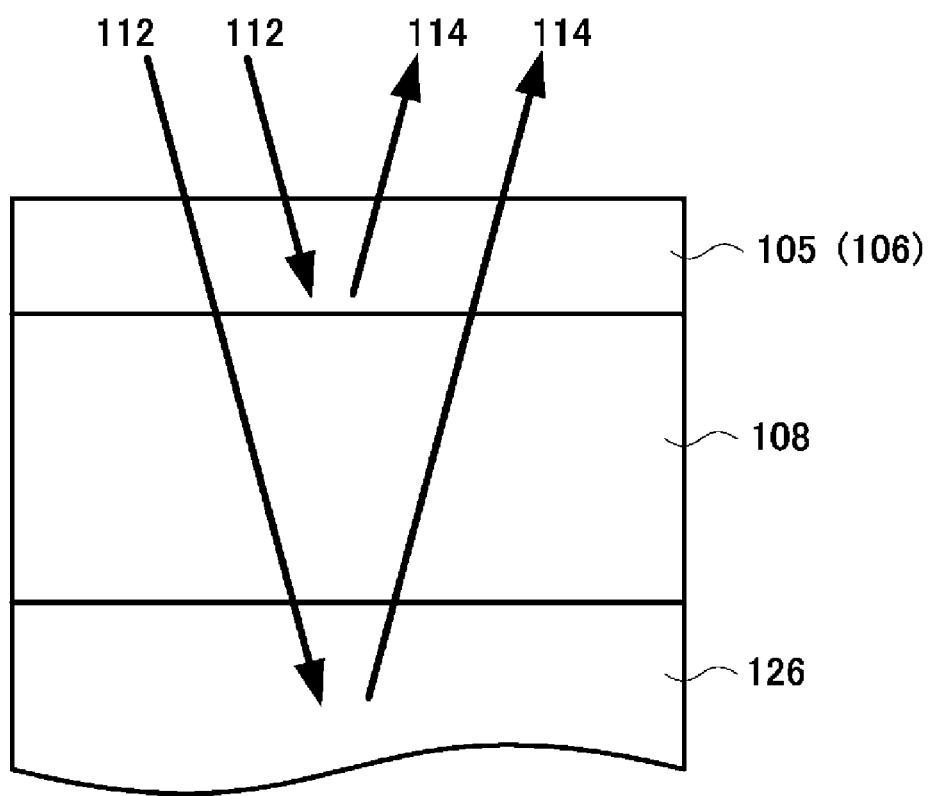
FIG. 6 is a cross sectional view showing an enlarged view of one example of a surface portion of the laminate substrate 110.

In the configuration example shown in FIG. 3, the measurement-target layer 106 includes the measurement-target laminate layer 104 that consists of a bilayer laminate structure formed of a first measurement-target monolayer 104*a* and a second measurement-target monolayer 104*b*. The second measurement-target monolayer 104*b* is positioned between the first measurement-target monolayer 104*a* and the absorption layer 108. In the configuration example shown in FIG. 4, the measurement-target layer 106 includes the measurement-target laminate layer 104 that consists of a bilayer laminate structure formed of the first measurement-target monolayer 104*a* and a third measurement-target monolayer 104*c*. The third measurement-target monolayer 104*c* is positioned closer to the surface than the first measurement-target monolayer 104*a* is. In the configuration example shown in FIG. 5, the measurement-target layer 106 includes the measurement-target laminate layer 104 that consists of a trilayer laminate structure formed of the first measurement-target monolayer 104*a*, the second measurement-target monolayer 104*b* and the third measurement-target monolayer 104*c*. The second measurement-target monolayer 104*b* is positioned between the first measurement-target monolayer 104*a* and the absorption layer 108, and the third measurement-target monolayer 104*c* is positioned closer to the surface than the first measurement-target monolayer 104*a* is. In the configuration example shown in FIG. 6, the measurement-target layer 106 includes the measurement-target monolayer 105. If the measurement-target layer 106 includes only the measurement-target monolayer 105, the configuration of the measurement-target layer 106 results in the same configuration as that of the measurement-target monolayer 105.

If the absorption layer 108 is a GaN layer for example, examples of the first measurement-target monolayer 104*a* may include an AlGaN layer that generates a 2DEG at a heterointerface of the absorption layer 108. In this case, examples of the second measurement-target monolayer 104*b* may include an AlN layer that functions as a spacer layer. Also, examples of the third measurement-target monolayer 104*c* may include a GaN layer or SiN layer (silicon nitride layer) that functions as a cap layer. If the third measurement-target monolayer 104*c* functions as a cap layer, the thickness of the third measurement-target monolayer 104*c* is preferably as small as possible. The third measurement-target monolayer 104*c* may be a p-type GaN layer that functions as an active layer of a normally-off transistor. If the third measurement-target monolayer 104*c* functions as an active layer of a normally-off transistor, a certain degree of thickness is necessary, and examples of such a thickness may include a thickness larger than that of the first measurement-target monolayer 104*a* for example. Because an AlGaN layer greatly affects the carrier concentration at a heterointerface, it is certainly necessary to measure the thickness and composition of the first measurement-target monolayer 104*a* with accuracy, and the thickness of a spacer layer also greatly affects the carrier concentration. For this reason, it is meaningful to measure the thickness and composition of the second measurement-target monolayer 104*b* with accuracy. Also, according to the measurement method of the present embodiment, measurement at many points is easy, and it is meaningful to be able to measure the distribution of the thickness and composition in a single wafer substrate in a short time also from the perspective of enhancing productivity.

The incident light 112 is light emitted toward the surface of the laminate substrate 110 on a side on which the measurement-target layer 106 is positioned, and the reflected light 114 is light that is generated from the incident light 112 reflecting off the laminate substrate 110.

The measurement method of the present embodiment includes emitting the incident light 112 toward the surface of the laminate substrate 110, and measuring the reflected light 114 of the incident light 112 from the laminate substrate 110 (S1). Among pieces of measurement data about the reflected light 114, mutually independent 2n or more pieces of data obtained at wavelengths which are equal to a threshold wavelength $\lambda\text{th}$ or shorter are extracted, and used as reflected light-related values (S2). Then, the reflected light-related values are used to calculate values related to the measurement-target layer 106, that is, values related to respective measurement-target monolayers included in the measurement-target layer 106 (the first measurement-target monolayer 104*a*, second measurement-target monolayer 104*b*, third measurement-target monolayer 104*c* and measurement-target monolayer 105) (S3).

In the calculation at S3, the thickness of each measurement-target monolayer included in the measurement-target layer 106 and a value related to the measurement-target monolayer can be calculated by curve fitting based on an analysis model. Specifically, a model of the measurement-target laminate layer 104 or the measurement-target monolayer 105 reflecting the layer structure of the measurement-target layer 106, that is, a model for each measurement-target monolayer is selected (s31), and a fitting parameter in the model is selected (s32). Fitting is performed such that the mean square error (MSE) between a theoretical value in the model and the measurement data is minimized (s33), and the thickness and composition of each measurement-target monolayer included in the measurement-target layer 106 can be determined.

Here, the threshold wavelength $\lambda\text{th}$ used is the maximum wavelength in a wavelength range over which the absolute value of a first-order derivative $dk(\lambda)/d\lambda$ obtained if the extinction coefficient k of the absorption layer 108 is expressed as a function $k(\lambda)$ of a wavelength $\lambda$ (expressed in nm) becomes equal to an extinction derivative threshold value or lower. The extinction derivative threshold value refers to a value defined to indicate where the extinction coefficient changes rapidly. The extinction derivative threshold value is preferably $1\times10^{-3}$, more preferably $5\times10^{-4}$, and further preferably $1\times10^{-4}$.

In normal film thickness measurement using ellipsometry, fitting targeted also at a reflected light-related value in an entire wavelength region, that is, a wavelength region exceeding the above-mentioned threshold wavelength $\lambda\text{th}$ is performed. Generally, a fringe caused by interference from a layer structure occurs in a long wavelength region exceeding $\lambda\text{th}$, and if the layer structure is complicated, it is often difficult to attain convergence to a proper value in fitting calculation due to a complicated fringe reflecting such a layer structure. However, in the present embodiment, by selecting the threshold wavelength $\lambda\text{th}$ in the above-mentioned manner, and calculating a value related to the measurement-target layer 106 (value related to each measurement-target monolayer included in the measurement-target layer 106) using a reflected light-related value which is data in a wavelength equal to $\lambda\text{th}$ or shorter, it becomes possible to perform fitting using light with a wavelength including much information on a surface of the laminate substrate 110, that is, information on the measurement-target layer 106 positioned closer to the surface than the absorption layer 108 is. As a result, it becomes unnecessary to consider the layer structure of and below the absorption layer 108 in selecting a fitting model, and the model can be simplified. Also, it becomes easier to attain convergence to a proper value in performing the fitting, and additionally, the measurement throughput can be enhanced by shortening calculation time required to attain the convergence.

Mutually independent 2n (n is an integer equal to one or larger) or more reflected light-related values can be acquired in configurations like the ones listed below. (1) Fix the angle of incidence of the incident light 112, and acquire, as reflected light-related values, one or more values selected from two polarized components and reflectance of the reflected light 114 for 2n or more wavelengths. (2) Fix the angle of incidence of the incident light 112, and acquire, as reflected light-related values, two or more values selected from two polarized components and reflectance of the reflected light 114 for n or more wavelengths. (3) Measure the reflected light 114 for n or more angles of incidence of the incident light 112, and acquire, as reflected light-related values, two or more values selected from two polarized components and reflectance of the reflected light 114 for each angle of incidence. (Note that this is applicable only if n is two or more.) (4) Measure the reflected light 114 for 2n or more angles of incidence of the incident light 112, and acquire, as reflected light-related values, one or more values selected from two polarized components and reflectance of the reflected light 114 for each angle of incidence.

In the above-mentioned cases of (1) to (4) (if n=1, in the above-mentioned cases of (1), (2) and (4)), spectrometry is performed on the reflected light 114, and one or more spectral values selected from two spectral polarized components and spectral reflectance of the reflected light 114 can be acquired as reflected light-related values. In this case, using linearly polarized light as the incident light 112, the spectroscopic phase difference ($\Delta$) and spectral reflection amplitude ratio angle (tan $\Psi$) of s-polarized light and p-polarized light can be acquired as two spectral polarized components of the reflected light 114. Here, "spectral values" refer not to values in each wavelength (spectral element value) in a case where spectroscopy is performed on the reflected light 114, but refer to the overall spectral element values in the entire spectroscopy-target wavelength region.

If curve fitting based on an analysis model is used in the above-mentioned calculation in S3, when the layer count n of the measurement-target monolayers included in the measurement-target layer 106 is two or more, the analysis model employed can be an absorption model in which one or more measurement-target monolayers among the two or more measurement-target monolayers included in the measurement-target layer 106 absorb light in a specific excitation generating wavelength region. For example, if the measurement-target layer 106 has the layer configuration shown in FIG. 3 or FIG. 5, the absorption model mentioned above as the analysis model for the second measurement-target monolayer 104b can be employed.

Here, the specific excitation generating wavelength region is an absorption wavelength region in each measurement-target monolayer that is observed when a model is derived from the measurement-target layer 106 (a wavelength region over which the extinction coefficient k becomes 0.001 or higher), and is different for each measurement-target monolayer. The specific excitation generating wavelength region is different from an absorption wavelength region in a bulk crystal of a substance that constitutes a measurement-target monolayer (bulk absorption wavelength region), and the degree of difference often varies depending on the magnitude of stress that the measurement-target monolayer undergoes and its thickness. If a measurement-target monolayer is undergoing tensile stress, the specific excitation generating wavelength region tends to shift toward a longer wavelength side relative to the bulk absorption wavelength region, and if it is undergoing compressive stress, it tends to shift toward a short wavelength side. Deviation of a specific excitation generating wavelength region from a bulk absorption wavelength region tends to increase as the thickness of a measurement-target monolayer decreases, and if it is equal to a certain degree of thickness or larger, the deviation can sometimes be ignored.

If an absorption model is employed for the second measurement-target monolayer 104b, in the curve fitting in the above-mentioned calculation at S3, a value related to a monolayer that is manufactured under the same condition as that for the first measurement-target monolayer 104a which is determined in advance by preliminary measurement targeted at the monolayer (for example, the thickness of the monolayer, optical constants of the monolayer such as the refractive index and extinction coefficient) can be set to an initial value of a parameter related to the first measurement-target monolayer 104a. That is, a preliminary sample with only the first measurement-target monolayer 104a but without the second measurement-target monolayer 104b is prepared, the preliminary sample undergoes preliminary measurement at the above-mentioned steps of S1 to S3, and the film thickness, optical constant and the like of the first measurement-target monolayer 104a in the preliminary sample are determined. The values of the film thickness, optical constant and the like of the first measurement-target monolayer 104a in this preliminary sample are set to initial values of parameters of curve fitting in measurement in a case where there is the second measurement-target monolayer 104b. In this manner, using values of the first measurement-target monolayer 104a measured preliminarily as initial values, suitable initial values can be given, the appropriateness and precision of a fitting result can be improved, and a length of time until convergence in fitting calculation can be shortened.

Also, if an absorption model is employed for the second measurement-target monolayer 104b, in curve fitting in the above-mentioned calculation at S3, the thicknesses of the first measurement-target monolayer 104a and the second measurement-target monolayer 104b obtained by preliminary curve fitting targeted at the first measurement-target monolayer 104a and the second measurement-target monolayer 104b can be set to initial values of parameters related to the first measurement-target monolayer 104a and the second measurement-target monolayer 104b. Because according to experimental rules, a relatively good converge result can be obtained for a film thickness, among values related to each measurement-target monolayer obtained as a result of curve fitting, regardless of suitability of an analysis model, an approximate value of the film thickness is obtained by preliminary curve fitting, and this is set to an initial value. By employing such a configuration, it becomes possible to obtain a suitable initial value, and a suitable fitting result can be obtained in a short calculation time. Particularly, there is an effect of being able to, with good precision, obtain an energy value at an absorption edge which is one of parameters in an absorption model.

Examples of the analysis model may include a dielectric function model that satisfies the Kramers-Kronig relations. The dielectric function model may include parametric semiconductor models, the Tauc-Lorenz model, the Lorentz model, the Drude model or the Gaussian model. The analysis model used may be the Sellmeier model or Cauchy model used together with a model that satisfies the Kramers-Kronig relations.

If curve fitting based on an analysis model is used in the above-mentioned calculation in S3, when the layer count n of the measurement-target monolayers included in the measurement-target layer 106 is two or more, the analysis model employed may be a transmission model in which one or more measurement-target monolayers among two or more measurement-target monolayers included in the measurement-target layer 106 entirely transmit light in a measured wavelength region.

Examples of the measurement-target monolayers included in the measurement-target layer 106 (the first measurement-target monolayer 104a, second measurement-target monolayer 104b, third measurement-target monolayer 104c and measurement-target monolayer 105) and the absorption layer 108 may include, as mentioned above, those that consist of semiconductors or dielectrics having mutually different compositions. The semiconductors may be Group IV semiconductors or Group III-V compound semiconductors. Examples of the Group IV semiconductors may include semiconductors including one or more types of atom selected from C, Si, Ge and Sn, for example, $C_aSi_bGe_cSn_d$ ($0 \le a \le 1$, $0 \le b \le 1$, $0 \le c \le 1$, $0 \le d \le 1$, a+b+c+d=1). Examples of the Group III-V compound semiconductors may include compound semiconductors including one or more types of atom selected from B, Al, Ga and In which are Group III atoms and including one or more types of atom selected from N, P, As and Sb which are Group V atoms, for example, $Al_aGa_bIn_cP_dAs_eSb_f$ ($0 \le a \le 1$, $0 \le b \le 1$, $0 \le c \le 1$, $0 \le d \le 1$, $0 \le e \le 1$, $0 \le f \le 1$, a+b+c=1, d+e+f=1) and $B_aAl_bGa_cIn_dN$ ($0 \le a \le 1$, $0 \le b \le 1$, $0 \le c \le 1$, $0 \le d \le 1$, a+b+c+d=1). Examples of the dielectrics may include $SiO_2$, $Si_3N_4$, SiON, $InO_2$, $SnO_2$, $InSnO_2$, $ZnO_2$, $TiO_2$ and $Al_2O_3$. The semiconductors may be doped with impurities.

For example, the measurement-target layer 106 includes the first measurement-target monolayer 104a and the second measurement-target monolayer 104b, the second measurement-target monolayer 104b is positioned closer to the absorption layer 108 than the first measurement-target monolayer 104a is. Examples of the first measurement-target monolayer 104a may include $In_{x1}Al_{x2}Ga_{x3}N$ (x1+x2+x3=1), examples of the second measurement-target monolayer 104b may include $In_{z1}Al_{z2}Ga_{z3}N$ (z1+z2+z3=1), and the second measurement-target monolayer 104b may have a bandgap that is larger than the bandgap of the first measurement-target monolayer 104a. This layer configuration corresponds to the layer configuration shown as an example in FIG. 3.

Alternatively, the measurement-target layer 106 includes the first measurement-target monolayer 104a and the third measurement-target monolayer 104c, and the first measurement-target monolayer 104a is positioned closer to the absorption layer 108 than the third measurement-target monolayer 104c is. Examples of the first measurement-target monolayer 104a may include $In_{x1}Al_{x2}Ga_{x3}N$ (x1+x2+x3=1), examples of the third measurement-target monolayer 104c may include $In_{q1}Al_{q2}Ga_{q3}N$ (q1+q2+q3=1), and the third measurement-target monolayer 104c may have a bandgap that is smaller than the bandgap of the first measurement-target monolayer 104a. This layer configuration corresponds to the layer configuration shown as an example in FIG. 4. A layer configuration obtained by combining the above-mentioned layer configuration corresponding to FIG. 3 and layer configuration corresponding to FIG. 4, that is, a configuration corresponding to the layer configuration in FIG. 5 may be adopted.

Examples of the substance of the first measurement-target monolayer 104a may include $Al_{x2}Ga_{x3}N$ (x2+x3=1, 0<x2≤0.5), and in this case, examples of the substance of the second measurement-target monolayer 104b may include AlN, and examples of the substance of the third measurement-target monolayer 104c may include GaN. GaN as the third measurement-target monolayer 104c in some cases functions as a cap layer and in other cases may be a p-type GaN layer that functions as an active layer of a normally-off transistor. GaN that functions as a cap layer preferably has a smaller thickness, and a p-type GaN layer for a normally-off transistor preferably has a certain degree of thickness. Examples of the certain degree of thickness may include a thickness larger than the thickness of the first measurement-target monolayer for example.

Also, if the first measurement-target monolayer 104a consists of $In_{x1}Al_{x2}Ga_{x3}N$ (x1+x2+x3=1), examples of the substance of the third measurement-target monolayer 104c may include silicon nitride. The silicon nitride layer functions as a cap layer, and similar to a GaN layer functioning as a cap layer, its thickness is preferably smaller. The GaN layer and silicon nitride layer functioning as cap layers provide an effect of preventing etching of the first measurement-target monolayer 104a at a latter stage of film formation.

In the curve fitting based on an analysis model, the mixed crystal ratio of each measurement-target monolayer included in the measurement-target layer 106 can be calculated. Examples of the absorption layer 108 may include one that consists of $In_{y1}Al_{y2}Ga_{y3}N$ (y1+y2+y3=1), and has a bandgap that is smaller than the bandgap of the first measurement-target monolayer 104a.

If the layer count n of a measurement-target monolayer included in the measurement-target layer 106 is 1, that is, if a measurement-target monolayer other than the measurement-target monolayer 105 is not included in the measurement-target layer 106, the measurement-target monolayer 105 may be one that consists of $In_{x1}Al_{x2}Ga_{x3}N$ (x1+x2+x3=1). Examples of the measurement-target monolayer 105 may include one that consists of $Al_{x2}Ga_{x3}N$ (x2+x3=1, 0<x2≤0.5). In these cases, the mixed crystal ratio (values of x1, x2 and x3) of the measurement-target monolayer 105 can be calculated by curve fitting based on an analysis model. Examples of the absorption layer 108 may include one that consists of $In_{y1}Al_{y2}Ga_{y3}N$ (y1+y2+y3=1), and has a bandgap that is smaller than the bandgap of the measurement-target monolayer 105.

Specific examples of the absorption layer 108 may include one that consists of GaN. In this case, the threshold wavelength λth can be set to 370 nm. The thickness of the absorption layer 108 is preferably equal to or larger than the light penetrating depth at a wavelength at which a second-order derivative $d^2k(\lambda)/d\lambda^2$ becomes 0 if the extinction coefficient k of the absorption layer 108 is expressed as a function $k(\lambda)$ of a wavelength λ (expressed in nm). If the absorption layer 108 consists of GaN, the thickness of the absorption layer 108 is preferably set to 240 nm or larger. If the wavelength of light is $\lambda_0$, and the extinction coefficient at $\lambda_0$ is $k_0$, the light penetrating depth is expressed as $\lambda_0/4\pi k_0$. If the thickness of the absorption layer 108 is reduced, light at a wavelength of λth or shorter is not absorbed sufficiently at the absorption layer 108, and fringes appear in some cases. If fringes appear, the mean square error (MSE) in fitting increases, and a normal fitting result cannot be obtained in some cases. Accordingly, a certain degree of thickness or larger is necessary for the absorption layer 108, and from such a perspective, in the present embodiment, the above-mentioned condition (equal to or larger than the light penetrating depth at a wavelength at which $d^2k(\lambda)/d\lambda^2$ becomes 0) is presented as one example of preferred thicknesses of the absorption layer 108.

According to the above-mentioned measurement method for the laminate substrate 110, it becomes possible to apply a simple analysis model even if the layer configuration closer to the substrate side relative to the absorption layer 108 is complicated. Therefore, accurate and prompt measurement of thicknesses and compositions becomes possible for measurement-target monolayers included in the measurement-target layer 106 (the first measurement-target monolayer 104a, second measurement-target monolayer 104b, third measurement-target monolayer 104c and measurement-target monolayer 105). Also, in the above-mentioned measurement method, it is possible to confine the incident light 112 to a small region, and mapping measurement of the laminate substrate 110 can also be implemented easily. As a result of these, even if the laminate substrate 110 has a complicated base layer configuration, high-precision and high-throughput mapping measurement of the measurement-target layer 106 positioned at the proximity of a surface of the laminate substrate 110 becomes possible. Also, the above-mentioned measurement method can easily cope with measurement of a wafer substrate having a diameter of 150 mm or larger, for example a 6-inch substrate, 8-inch substrate or the like, by providing a suitable substrate moving mechanism such as a substrate stage.

Example 1

As Example 1, a case where the layer count n of a measurement-target monolayer included in the measurement-target layer 106 is one is explained. As a sample substrate for measurement, a sample laminate substrate similar to the laminate substrate 110 shown in FIG. 2 and FIG. 6 was prepared. A Si (111) substrate was used as the base substrate 102, and an AlN layer and an AlGaN layer were formed as the intermediate layer 120. As the buffer layer 126, a 5 nm-thick AlN layer and a 25 nm-thick AlGaN layer were laminated one on another 100 times to form a superlattice buffer. As the absorption layer 108, a 1000 nm-thick GaN layer was formed. As the measurement-target monolayer 105 (measurement-target layer 106), a monolayer, $Al_{0.25}Ga_{0.75}N$ layer, was formed. The thickness of the $Al_{0.25}Ga_{0.75}N$ layer was 25 nm (design value). The Al composition 0.25 of the $Al_{0.25}Ga_{0.75}N$ layer was a design value.

For the prepared sample laminate substrate for measurement, the incident light 112 including light with a shorter wavelength than a threshold wavelength is emitted toward a surface of the sample laminate substrate (laminate substrate 110) on a side on which the $Al_{0.25}Ga_{0.75}N$ layer which is the measurement-target monolayer 105 (measurement-target layer 106) is positioned, and the reflected light 114 of the incident light 112 from the sample laminate substrate (laminate substrate 110) was measured; thereby, mutually independent two (because n is 1 in Example 1, 2n=2) or more pieces of spectroscopic ellipsometric data (reflected light-related values) were acquired for wavelengths equal to a threshold wavelength or shorter. Thereafter, using this spectroscopic ellipsometric data (reflected light-related values), the film thickness and composition (values related to the measurement-target monolayer 105 included in the measurement-target layer 106) about the $Al_{0.25}Ga_{0.75}N$ layer (the measurement-target monolayer 105) were calculated. The threshold wavelength ($\lambda$th) used was 370 nm (the maximum wavelength in a wavelength range over which the absolute value of a first-order derivative $dk(\lambda)/d\lambda$ obtained if the extinction coefficient k of the GaN layer which is the absorption layer 108 is expressed as a function $k(\lambda)$ of a wavelength $\lambda$ (expressed in nm) becomes equal to an extinction derivative threshold value or lower).

Figure 7:
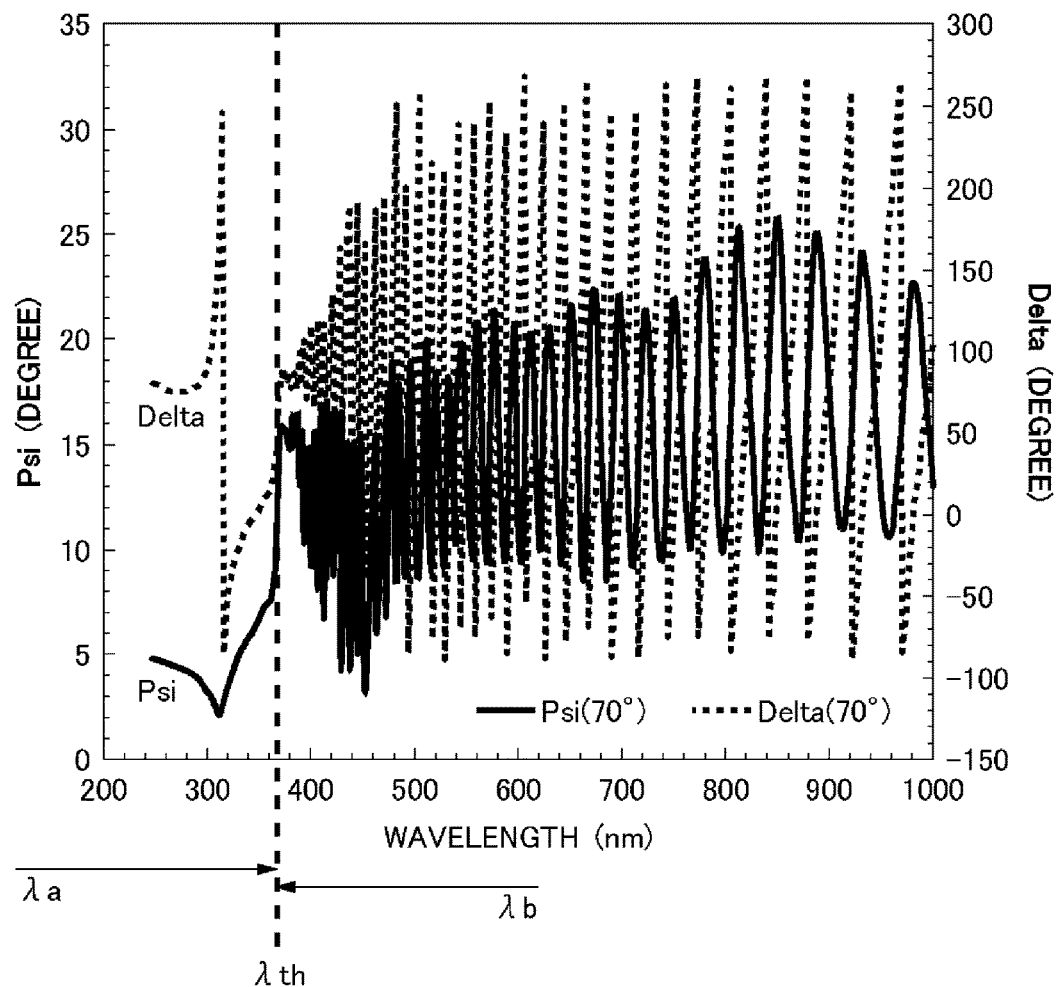
FIG. 7 is a chart showing spectroscopic ellipsometric data of a sample laminate substrate for an entire wavelength region.

FIG. 7 is a chart showing spectroscopic ellipsometric data of the sample laminate substrate for an entire wavelength region. The solid line indicates the reflection amplitude ratio angle $\Psi$ of p-polarized light and s-polarized light, and the dotted line indicates the phase difference $\Delta$. In the wavelength region $\lambda$b equal to $\lambda$th (about 370 nm) or longer, periodical variation (fringes) of $\Psi$ and $\Delta$ appear, reflecting a complicated structure of and below the buffer layer. A complicated analysis model is necessary for performing fitting using such complicated spectral data, and analysis becomes difficult.

Figure 8:
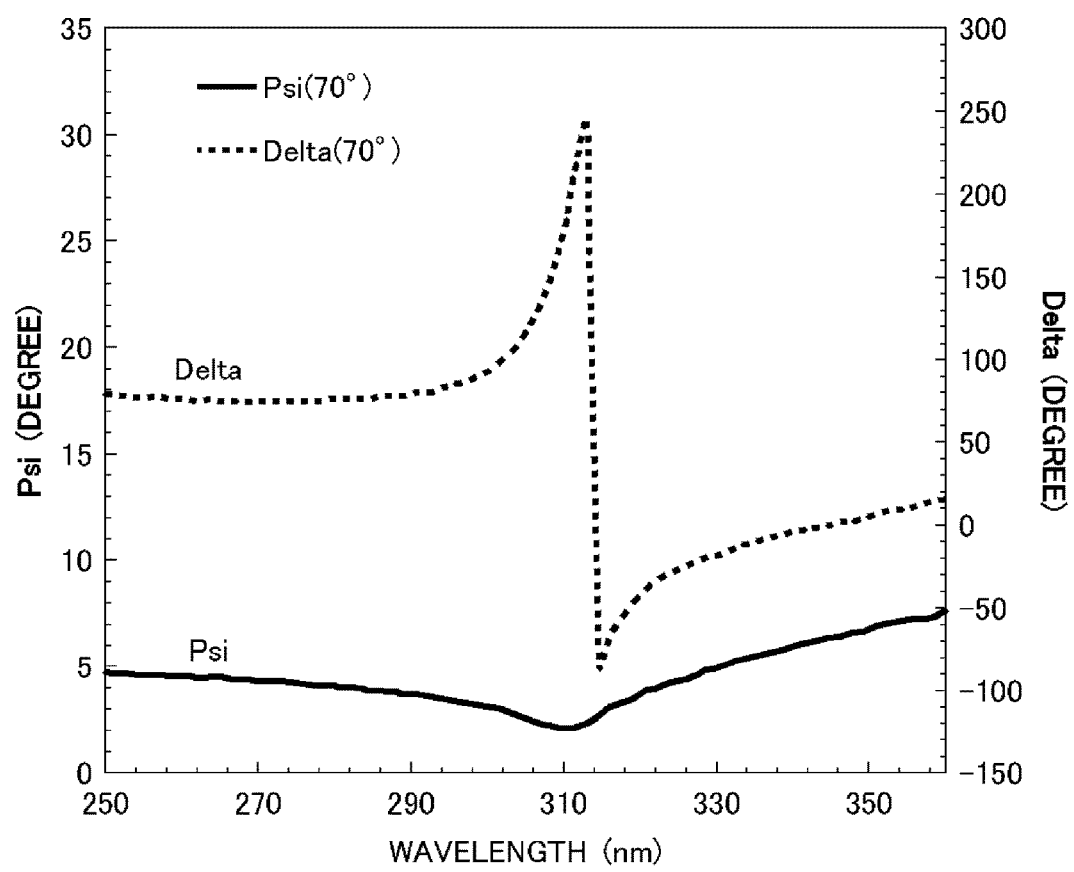
FIG. 8 is a chart showing spectroscopic ellipsometric data for a wavelength region λa in FIG. 7.

FIG. 8 is a chart showing spectroscopic ellipsometric data for the wavelength region $\lambda$a in FIG. 7. In the present invention, analysis is performed using only spectral data in the wavelength region $\lambda$a which is equal to $\lambda$th or shorter. For this reason, the analysis model can be simplified, and the analysis can be made easy to perform. As a layer configuration of the analysis model, a sufficiently thick GaN layer (the absorption layer 108), an $Al_xGa_{1-x}N$ layer which is the measurement-target monolayer 105, and a roughness layer of a surface of the $Al_xGa_{1-x}N$ layer were employed. An effective medium approximation model in which AlGaN and air are mixed at a ratio of 0.5:0.5 was employed for the roughness layer, an alloy model prepared by interpolation between pieces of data based on references with different Al compositions x was employed for the measurement-target monolayer 105, and a parametric semiconductor model and the Tauc-Lorenz model were employed as individual optical models.

Figure 9:
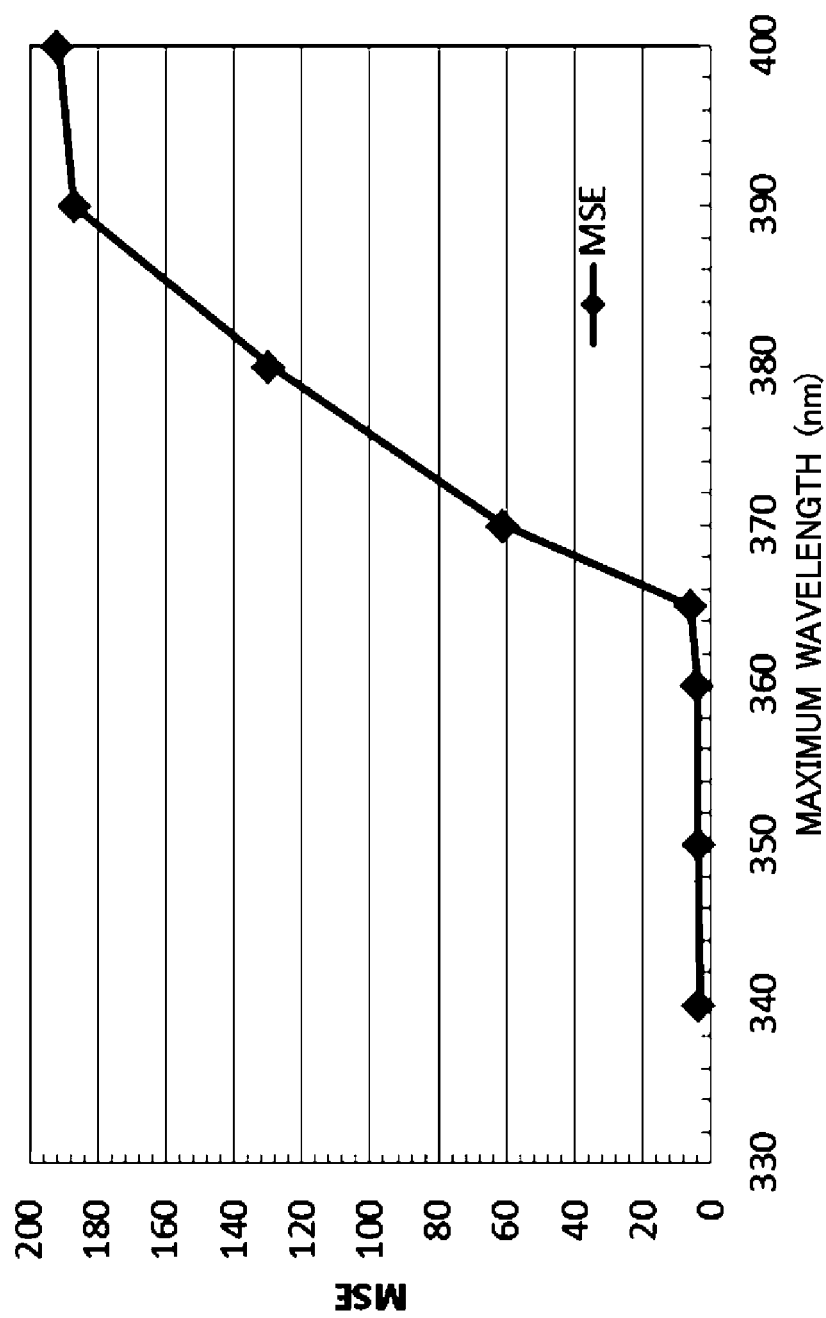
FIG. 9 is a chart showing a fitting result obtained with various wavelength region upper limits of spectroscopic ellipsometric data used in analysis.
Figure 10:
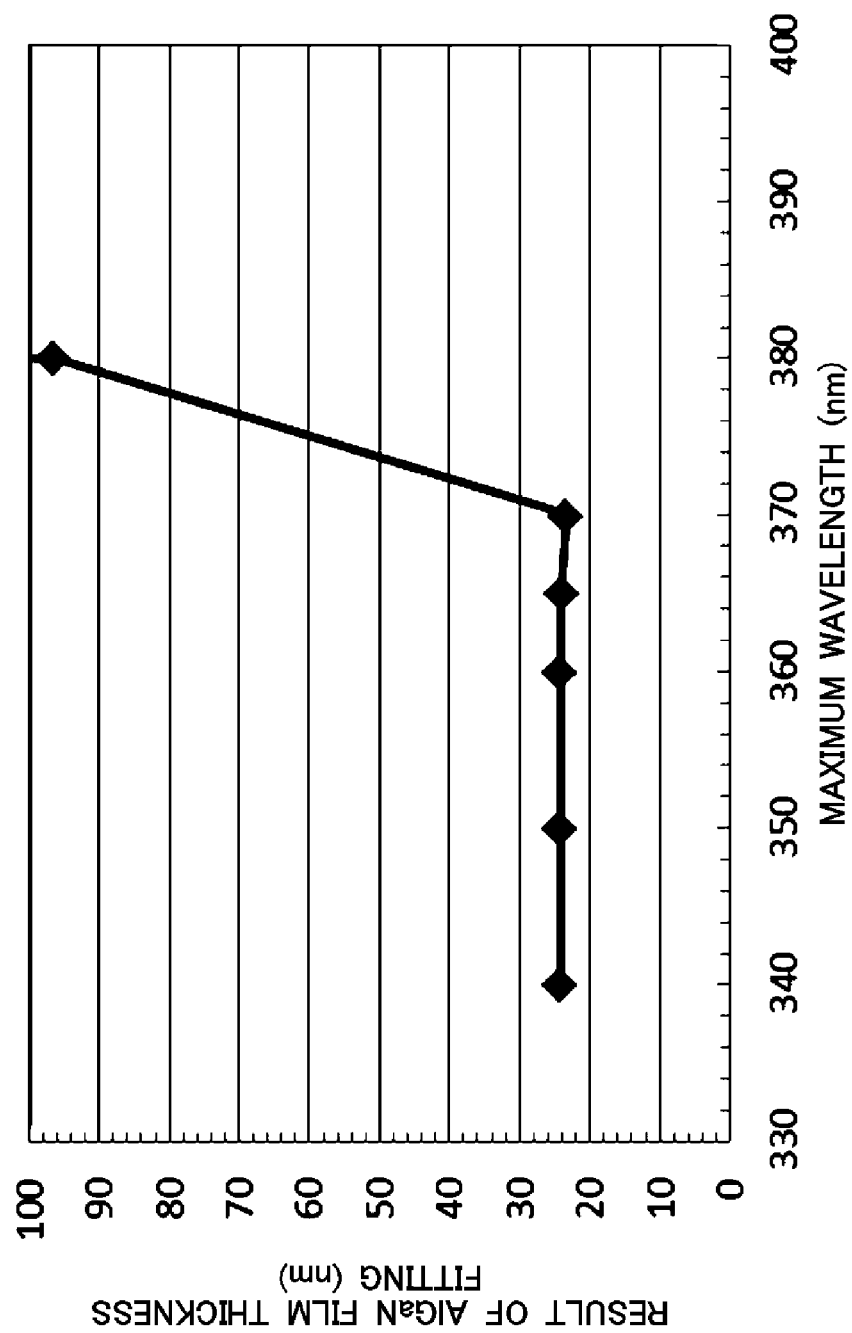
FIG. 10 is a chart showing a fitting result obtained with various wavelength region upper limits of spectroscopic ellipsometric data used in analysis.
Figure 11:
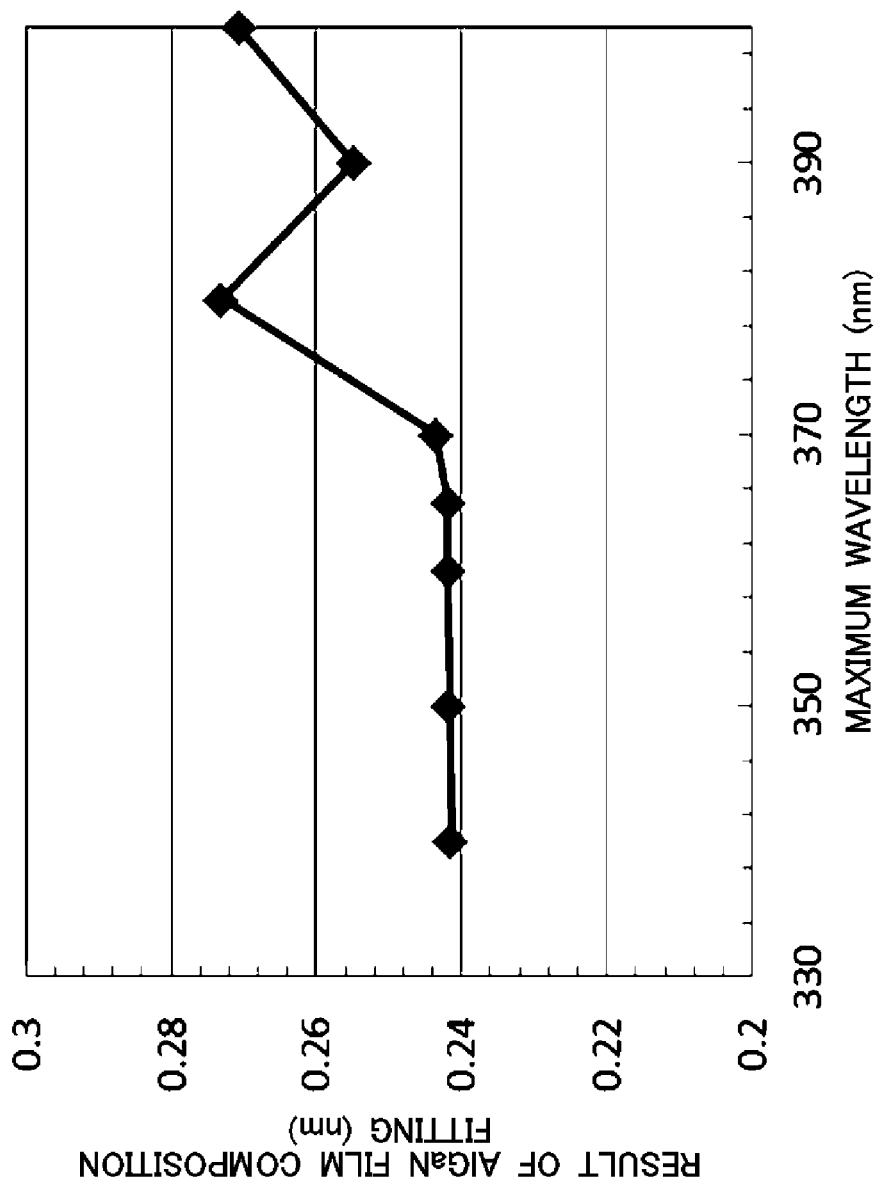
FIG. 11 is a chart showing a fitting result obtained with various wavelength region upper limits of spectroscopic ellipsometric data used in analysis.

FIG. 9 to FIG. 11 are charts showing fitting results obtained with various wavelength region upper limits of spectroscopic ellipsometric data used in analysis. FIG. 9 shows the mean square error (MSE), FIG. 10 shows the film thickness of the measurement-target monolayer 105, and FIG. 11 shows the Al composition x of the measurement-target monolayer 105. The charts show analysis results in which the MSE in a case where fitting was performed using data of wavelength regions exceeding 370 nm exceeds 100, and both the film thickness and the composition deviated greatly from an actual thickness and composition. In contrast to this, if fitting was performed using data of wavelength regions of 370 nm or shorter, the MSE was small, both the film thickness and the composition indicated values close to an actual film thickness and composition, and it can be known that the analysis was successful. From the results above, it could be known that by performing fitting using spectroscopic ellipsometric data of wavelength regions of 370 nm or shorter, the thickness and composition of the measurement-target monolayer 105 can be measured with accuracy.

Figure 12:
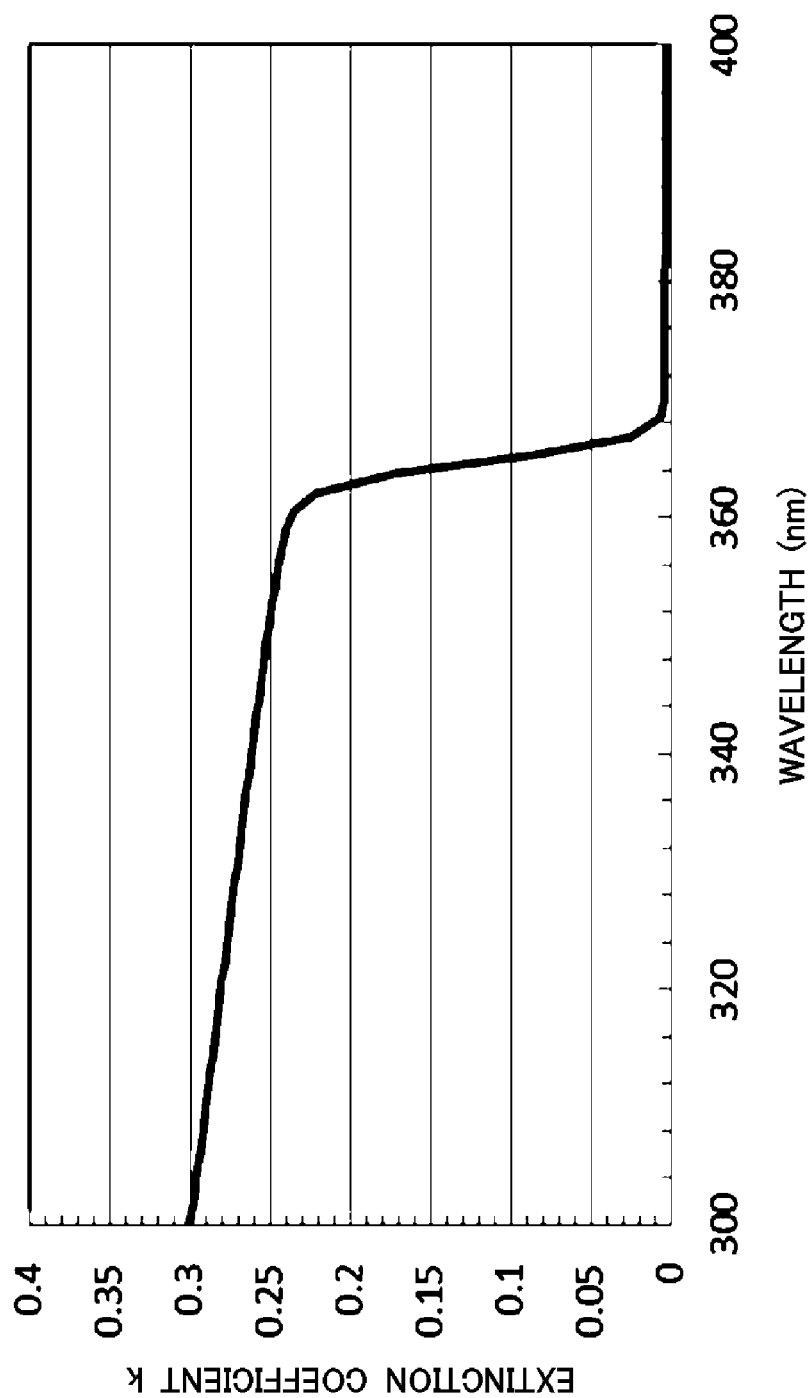
FIG. 12 is a chart showing a relation between the extinction coefficient of a GaN layer which is an absorption layer and a wavelength.
Figure 13:
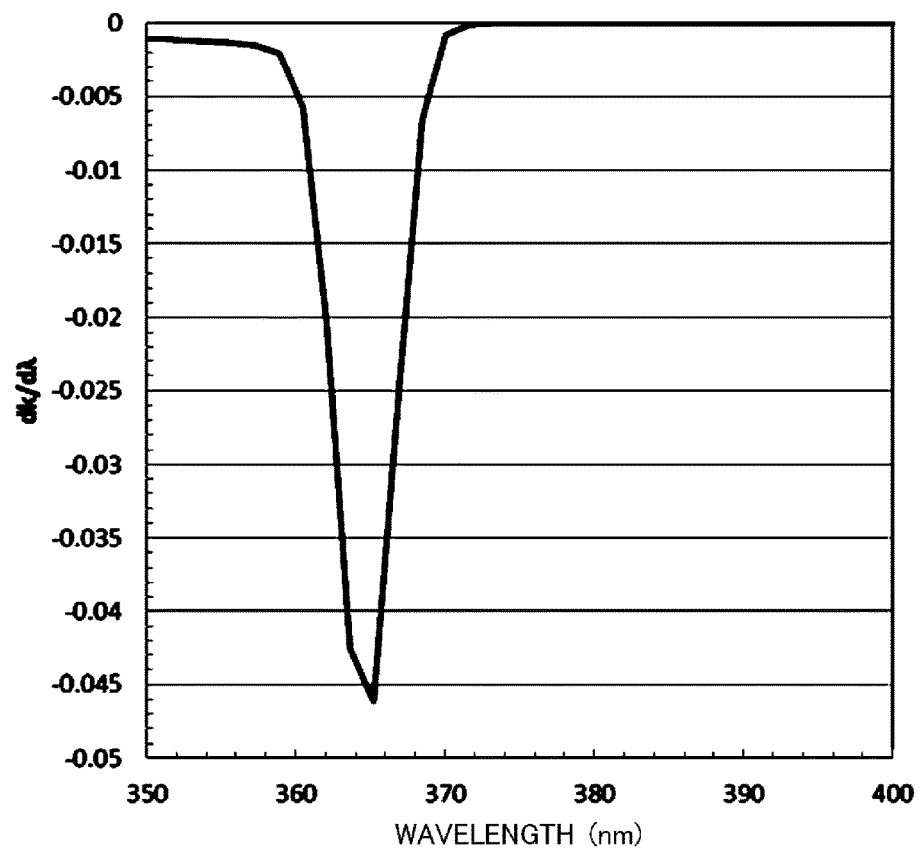
FIG. 13 is a chart obtained by first-order differentiation, at each wavelength, of the extinction coefficient of a GaN layer which is an absorption layer.

FIG. 12 is a chart showing a relation between the extinction coefficient k of a GaN layer which is the absorption layer 108 and a wavelength $\lambda$, and FIG. 13 is a chart showing a result obtained by first-order differentiation $(dk/d\lambda)$ of the extinction coefficient k at each wavelength $\lambda$. It could be known that the wavelength at which the extinction coefficient becomes $-1\times10^{-4}$ or lower is 370 nm, and matches the threshold wavelength.

Figure 14:
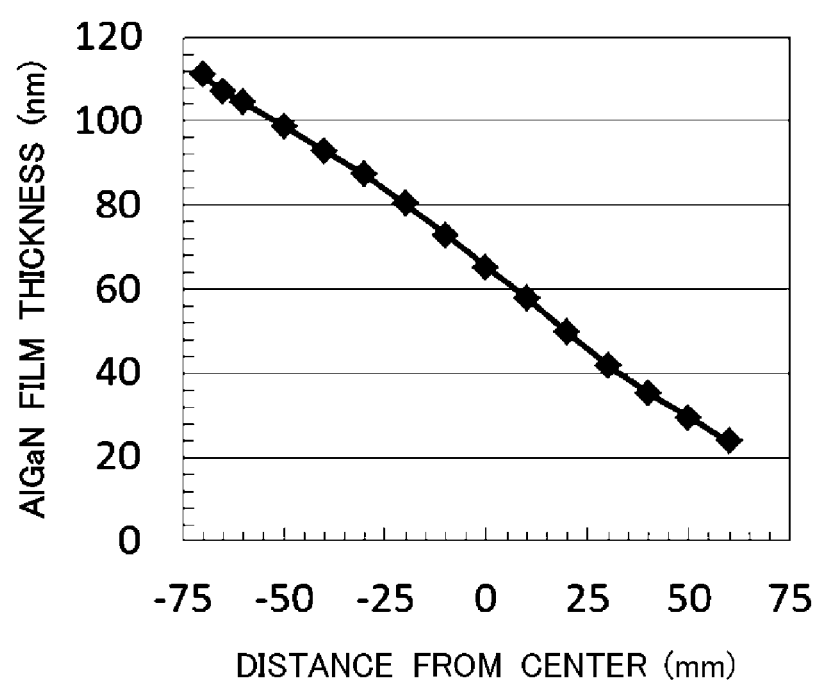
FIG. 14 is a chart showing an example in which measurement was performed at various positions in a substrate plane.
Figure 15:
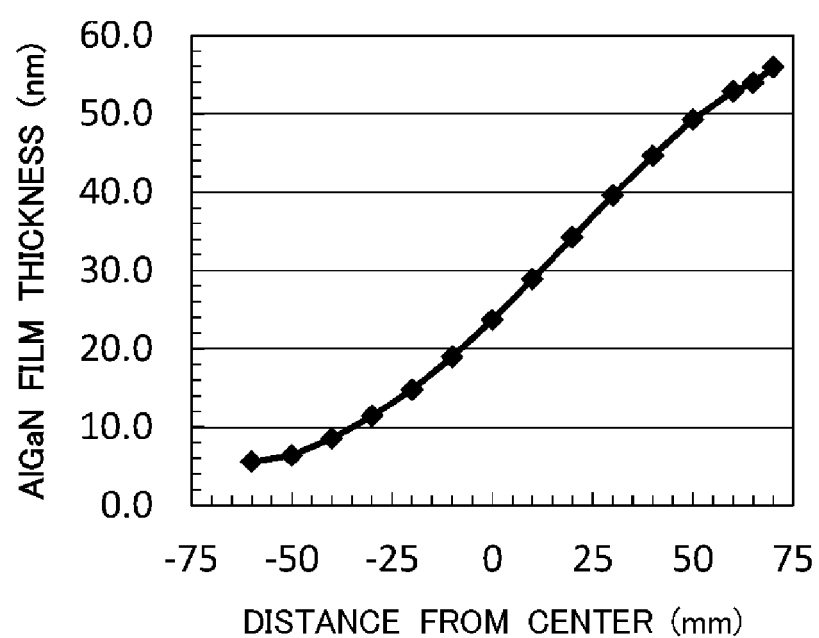
FIG. 15 is a chart showing an example in which measurement was performed at various positions in a substrate plane.

FIG. 14 and FIG. 15 are charts showing examples obtained by measurement on a sample in which the thickness of an AlGaN layer which is the measurement-target monolayer 105 varies greatly in the substrate plane, that is, the film thickness distribution is large, at different positions in the substrate plane. By putting together the two examples shown in FIG. 14 and FIG. 15, it can be known that the film thickness could be measured with accuracy in the range from the smallest film thickness of 5.6 nm to the largest film thickness of 111 nm. Also, as can be read out from the horizontal axes of FIG. 14 and FIG. 15, measurement was performed with accuracy in the diameter range of about 150 mm (about 6 inches).

Figure 16:
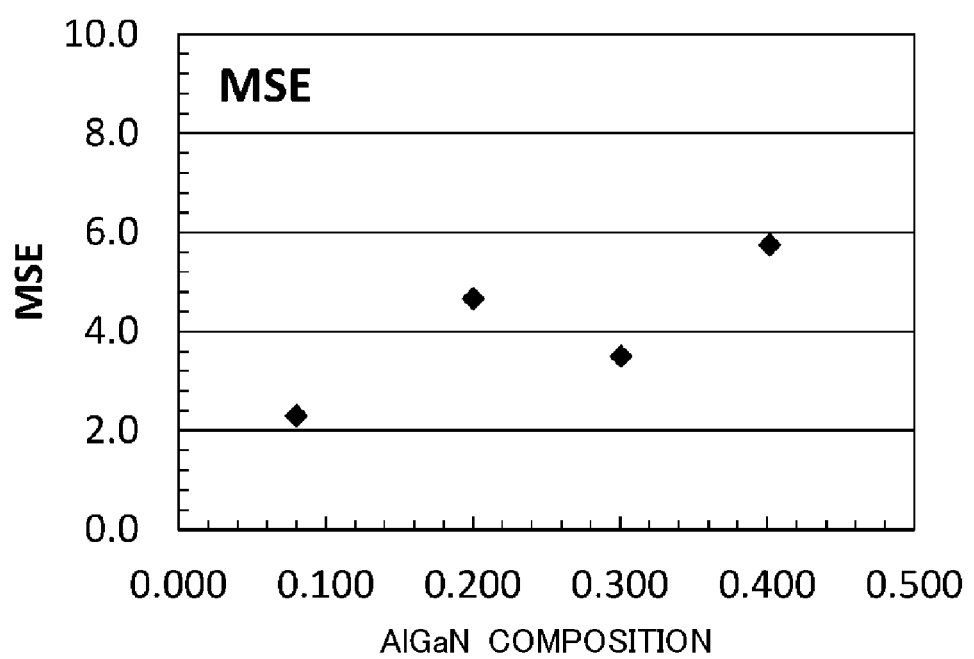
FIG. 16 is a chart showing changes in MSE with various Al compositions of an AlGaN layer which is a measurement-target layer.

FIG. 16 is a chart showing changes in MSE with various Al compositions of an AlGaN layer which is the measurement-target monolayer 105. It can be known that even if the Al composition varies in the range of 0.08 to 0.402, it could be measured with accuracy.

Figure 17:
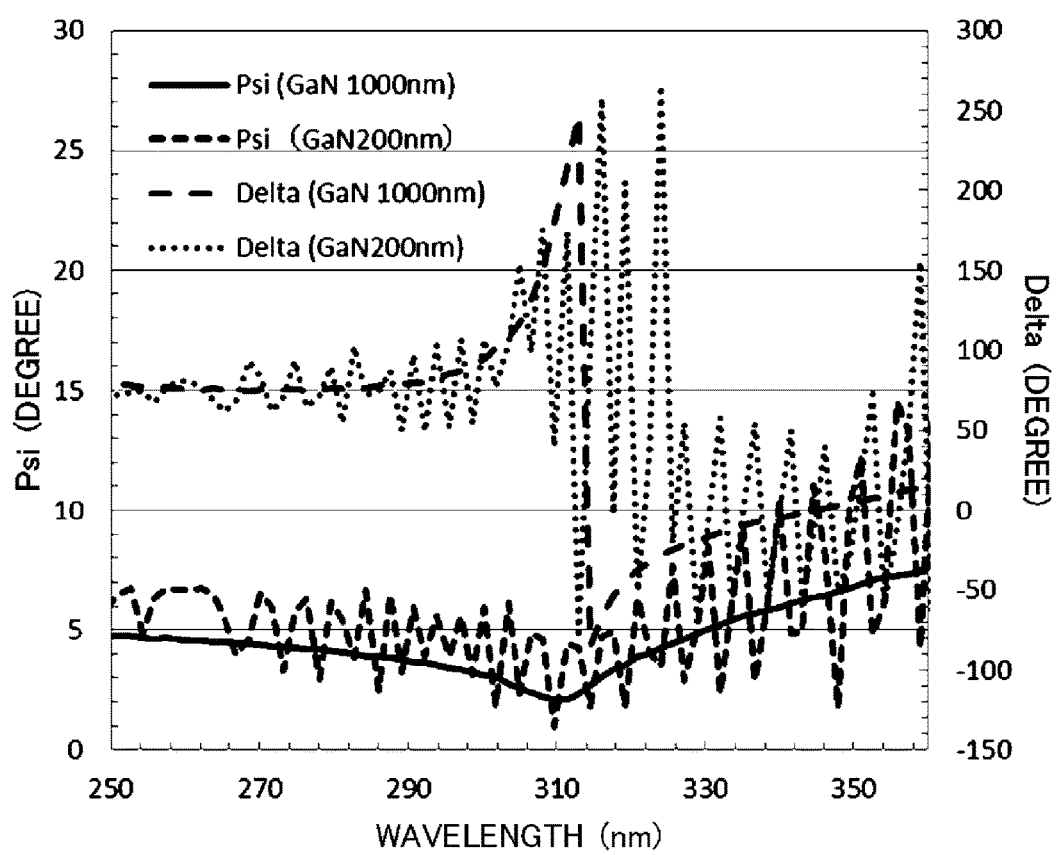
FIG. 17 is a chart showing spectroscopic ellipsometric data obtained if the thickness of a GaN layer which is an absorption layer was set to 1000 nm and 200 nm.

FIG. 17 is a chart showing spectroscopic ellipsometric data obtained if the thickness of the GaN layer which is the absorption layer 108 was set to 1000 nm and 200 nm. It can be known that if the thickness of the absorption layer 108 is reduced, light at a wavelength of $\lambda$th or shorter cannot be fully absorbed at the absorption layer, and fringes appear. Because if fringes appear, the mean square error (MSE) in fitting increases, and a normal fitting result cannot be obtained; therefore, a certain degree of thickness or larger is necessary for the absorption layer 108.

Figure 18:
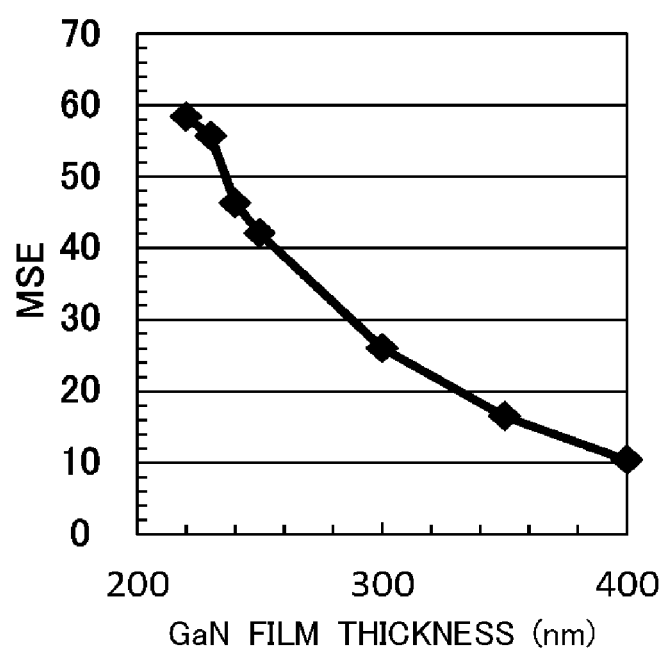
FIG. 18 is a chart showing a fitting result obtained with various thicknesses of a GaN layer which is an absorption layer.
Figure 19:
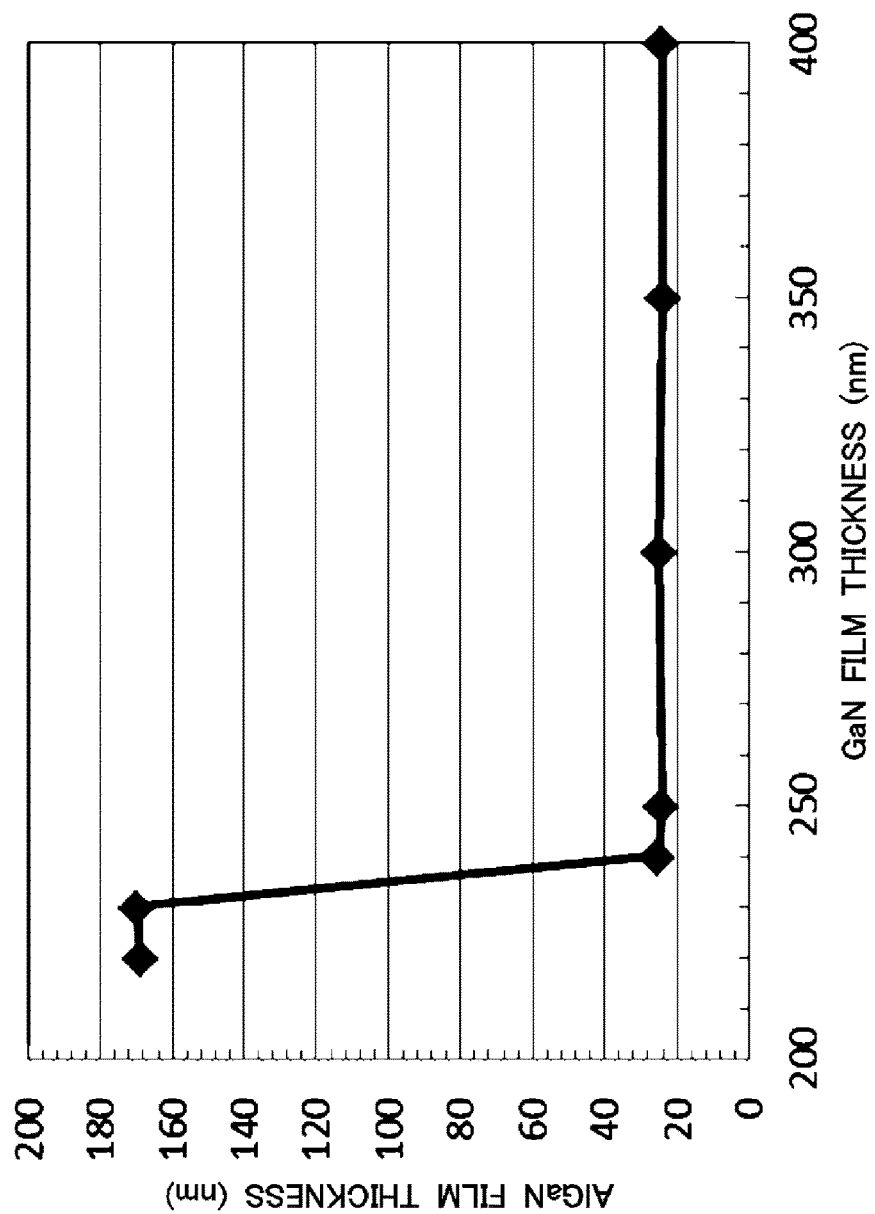
FIG. 19 is a chart showing a fitting result obtained with various thicknesses of a GaN layer which is an absorption layer.
Figure 20:
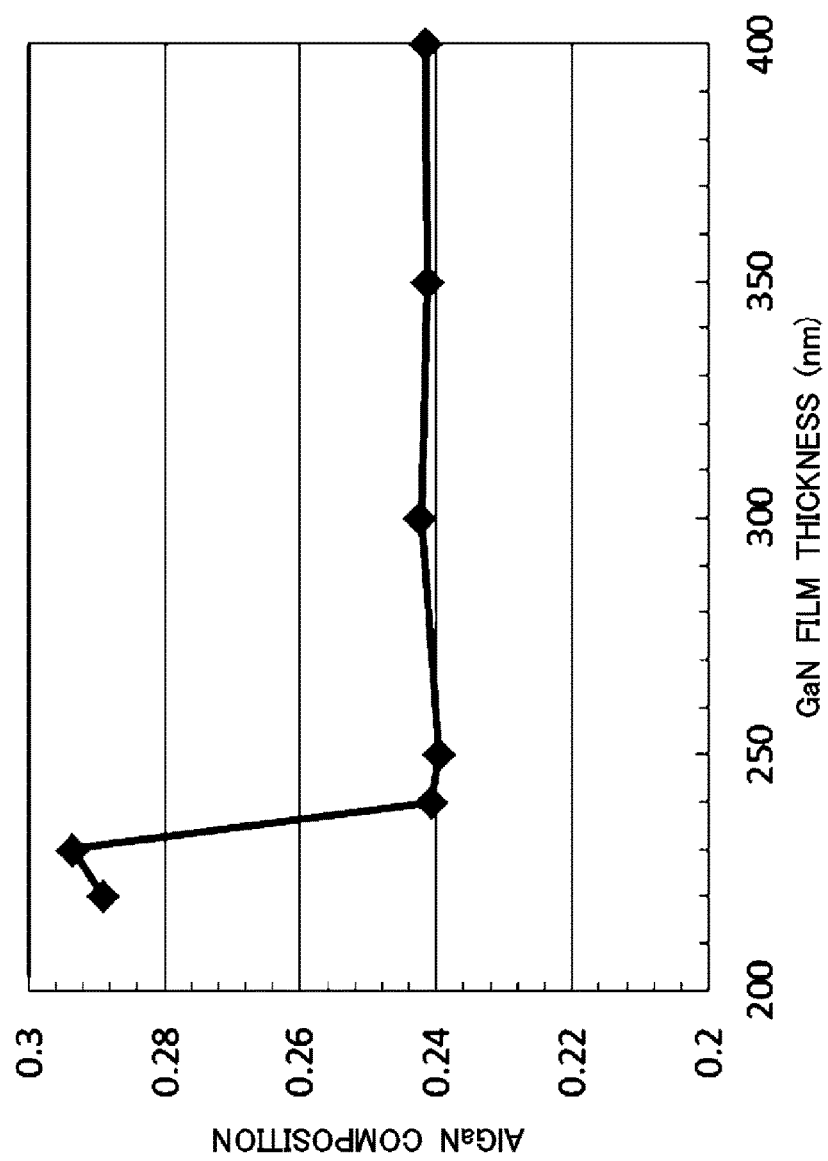
FIG. 20 is a chart showing a fitting result obtained with various thicknesses of a GaN layer which is an absorption layer.

FIG. 18 to FIG. 20 are charts showing fitting results obtained with various thicknesses of a GaN layer which is the absorption layer. FIG. 18 shows the mean square error (MSE), FIG. 19 shows the film thickness of the measurement-target monolayer 105, and FIG. 20 shows the Al composition x of the measurement-target monolayer 105. From the results in FIG. 18 to FIG. 20, the thickness of the GaN layer needs to be 240 nm or larger.

Figure 21:
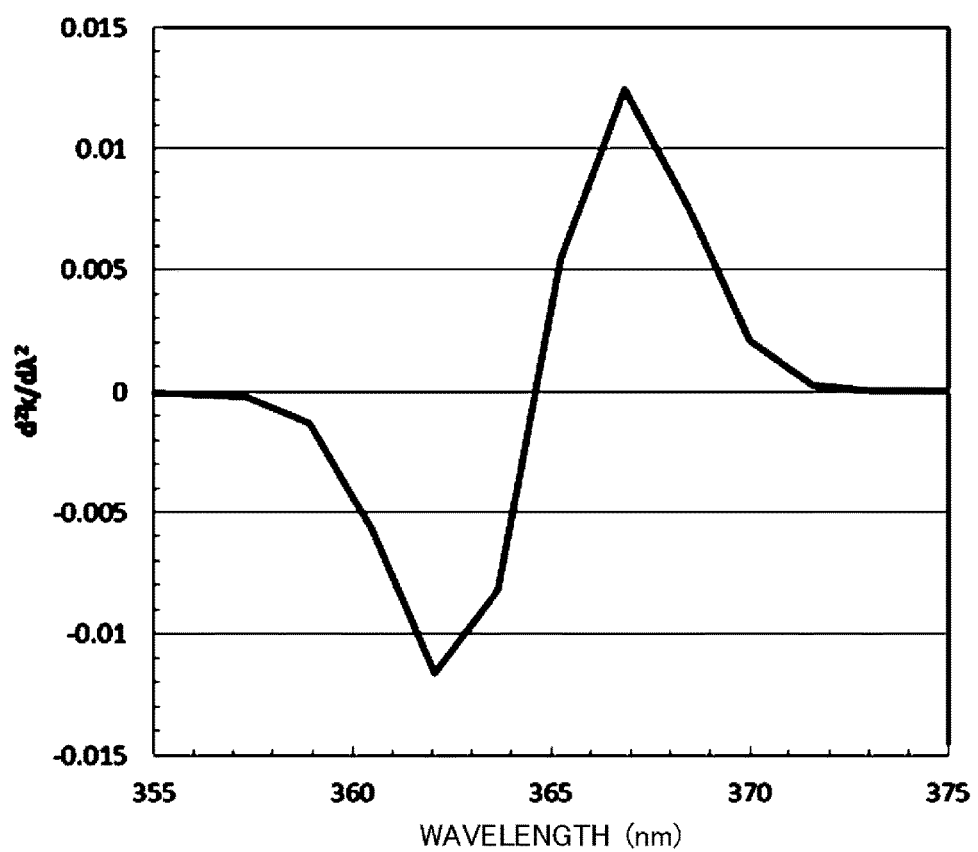
FIG. 21 is a chart obtained by second-order differentiation, at each wavelength, of the extinction coefficient of a GaN layer which is an absorption layer.

FIG. 21 is a chart showing a result obtained by second-order differentiation ($d^2k/d\lambda^2$) of the extinction coefficient k of the GaN layer which is the absorption layer at each wavelength $\lambda$. The wavelength at which a second-order derivative becomes zero is 364.6 nm, and judging from FIG. 21, the extinction coefficient at 364.6 nm is 0.12. As a result of calculation, the light penetrating depth at this wavelength is 242 nm, and matches the film thickness necessary for the GaN layer.

Example 2

As Example 2, a case where the layer count n of measurement-target monolayers included in the measurement-target layer 106 is two is explained. As a sample substrate for measurement of Example 2, a sample laminate substrate similar to the laminate substrate 110 shown in FIG. 2 and FIG. 3 was prepared. The base substrate 102, the intermediate layer 120, the buffer layer 126 and the absorption layer 108 are similar to those in Example 1. In Example 2, an AlN layer which is the second measurement-target monolayer 104b was formed as a spacer layer between a GaN layer which is the absorption layer 108 and an $Al_{0.25}Ga_{0.75}N$ layer which is the first measurement-target monolayer 104a. That is, the measurement-target layer 106 that consists of the $Al_{0.25}Ga_{0.75}N$ layer (the first measurement-target monolayer 104a) and the AlN layer (the second measurement-target monolayer 104b) was formed. The thicknesses of the AlN layer prepared were 0 nm (no AlN layer), 0.5 nm, 1 nm and 2 nm.

Similar to Example 1, in measurement of the sample laminate substrate of Example 2, it was irradiated with the incident light 112, spectroscopic ellipsometric data was acquired from the reflected light 114, and the film thicknesses and compositions of the $Al_{0.25}Ga_{0.75}N$ layer and AlN layer (the respective measurement-target monolayers included in the measurement-target layer 106) were calculated using the spectroscopic ellipsometric data. The threshold wavelength ($\lambda$th) used was 370 nm. Note that an absorption model was applied to an analysis model in fitting of the AlN layer (the second measurement-target monolayer 104b).

If the sample laminate substrate of Example 2 is analyzed, the thicknesses and compositions of the $Al_{0.25}Ga_{0.75}N$ layer and the AlN layer (the first measurement-target monolayer 104a and the second measurement-target monolayer 104b) should each be able to be measured by implementing fitting similar to that in Example 1 if an alloy model corresponding to the AlN layer is added in the analysis model of Example 1.

Figure 22:
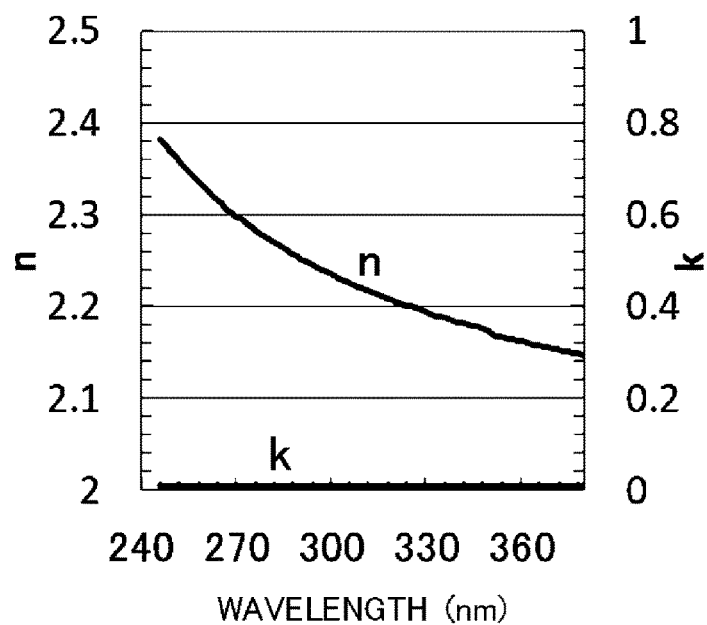
FIG. 22 shows optical properties of a transparent model.
Figure 23:
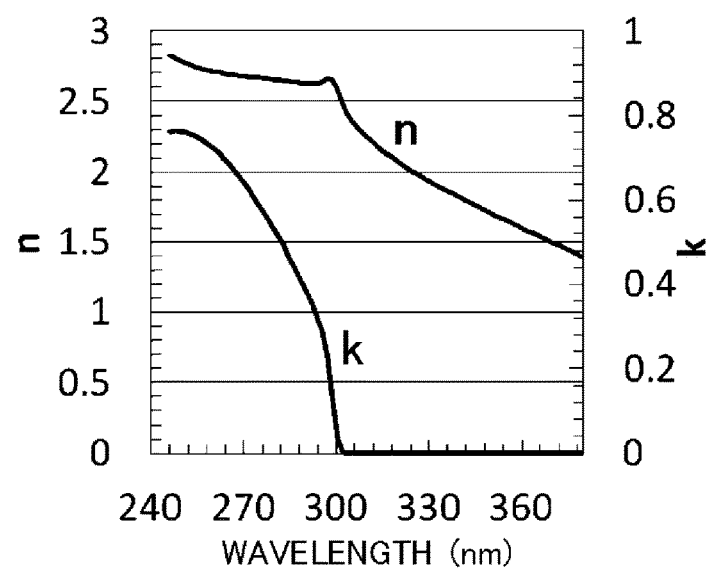
FIG. 23 shows optical properties of an absorption model.

However, errors became larger if a transparent model having optical properties as shown in FIG. 22 was employed as an optical model for the AlN layer. In view of this, an absorption model in which absorption occurs even in a wavelength region where absorption does not occur intrinsically with bulk AlN (absorption model in which light is absorbed in a specific excitation generating wavelength region) was employed to perform analysis. The optical properties in the absorption model are shown in FIG. 23.

Figure 24:
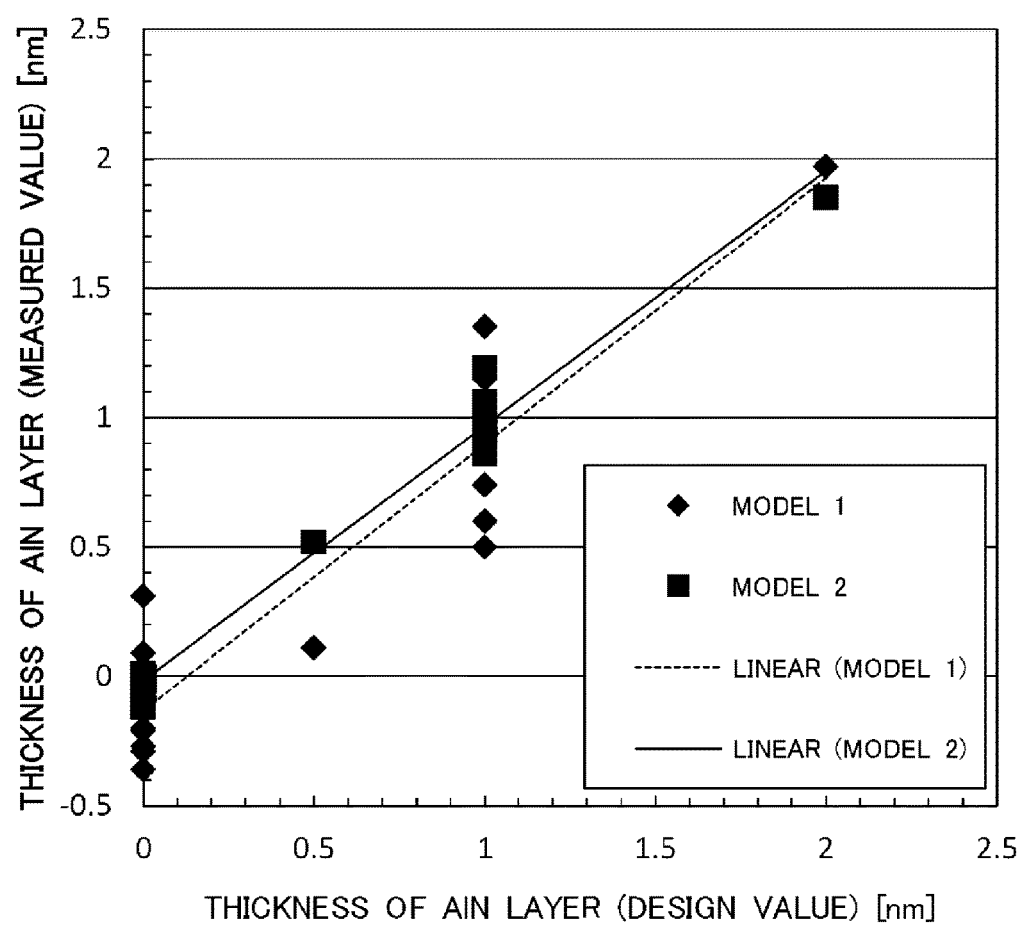
FIG. 24 is a correlation chart showing a result of thicknesses of AlN layers obtained if measurement was implemented on sample laminate substrates with AlN layers having different thicknesses.

FIG. 24 is a correlation chart showing a result of the thickness of the AlN layer obtained by implementing the above-mentioned measurement for sample laminate substrates having different AlN layer thicknesses which are equal to 0 (no AlN layer), 0.5 nm, 1 nm and 2 nm. The horizontal axis indicates design values, and the vertical axis indicates measured values. The diamond-shaped plots indicate a result obtained if a transparent model is applied to the AlN layer (model 1), and the square-shaped plots indicate a result obtained if an absorption model is applied to the AlN layer (model 2). In the model 1, 3$\sigma$=0.64 if the thickness of the AlN layer was 0 nm, and 3$\sigma$=0.92 if the thickness of the AlN layer was 1 nm. In the model 2, 3$\sigma$=0.13 if the thickness of the AlN layer was 0 nm, and 3$\sigma$=0.32 if the thickness of the AlN layer was 1 nm. It is obvious from the results shown in FIG. 24 that errors are smaller if an absorption model is employed.

Example 3

As Example 3, a case where the layer count n of measurement-target monolayers included in the measurement-target layer 106 is two is explained. As a sample substrate for measurement of Example 3, a sample laminate substrate similar to the laminate substrate 110 shown in FIG. 2 and FIG. 4 was prepared. The base substrate 102, the intermediate layer 120, the buffer layer 126 and the absorption layer 108 are similar to those in Example 1. In Example 3, a 1 nm-thick GaN layer (the third measurement-target monolayer 104c) was formed as a cap layer on an $Al_{0.25}Ga_{0.75}N$ layer which is the first measurement-target monolayer 104a. That is, the measurement-target layer 106 that consists of the $Al_{0.25}Ga_{0.75}N$ layer (the first measurement-target monolayer 104a) and the GaN layer (the third measurement-target monolayer 104c) was formed.

Similar to Example 1, in measurement of the sample laminate substrate of Example 3, it was irradiated with the incident light 112, spectroscopic ellipsometric data was acquired from the reflected light 114, and the film thicknesses and compositions of the $Al_{0.25}Ga_{0.75}N$ layer and GaN layer (the respective measurement-target monolayers included in the measurement-target layer 106) were calculated using the spectroscopic ellipsometric data. The threshold wavelength (λth) used was 370 nm. Note that an absorption model was applied to an analysis model in fitting of the GaN layer (the third measurement-target monolayer 104c).

If the sample laminate substrate of Example 3 is analyzed, the thicknesses and compositions of the $Al_{0.25}Ga_{0.75}N$ layer and the GaN layer (the first measurement-target monolayer 104a and the third measurement-target monolayer 104c) should each be able to be measured by implementing acquisition of spectroscopic ellipsometric data and fitting similar to those in Example 1 if an alloy model corresponding to the GaN layer is added in the analysis model of Example 1.

Figure 25:
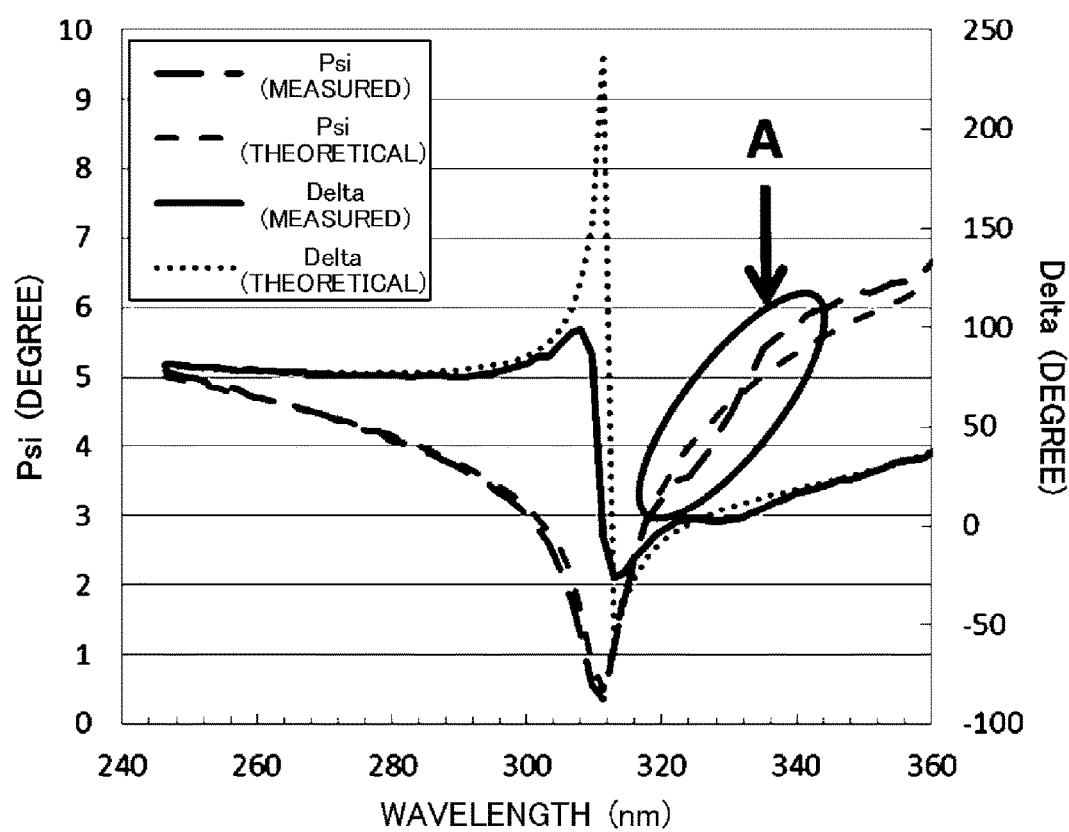
FIG. 25 is a chart showing theoretical values calculated from a model and spectroscopic ellipsometric data obtained by measurement.

However, if an absorption model similar to an absorption model in which absorption occurs in bulk GaN is employed as an optical model of the GaN layer, mismatch occurs between theoretical values calculated from the model and measured spectroscopic ellipsometric data as shown in FIG. 25. This mismatch is large at a part where a kink occurs indicated with A in the figure, and occurrence of such a kink indicates that there are changes in the absorption coefficient k.

Figure 26:
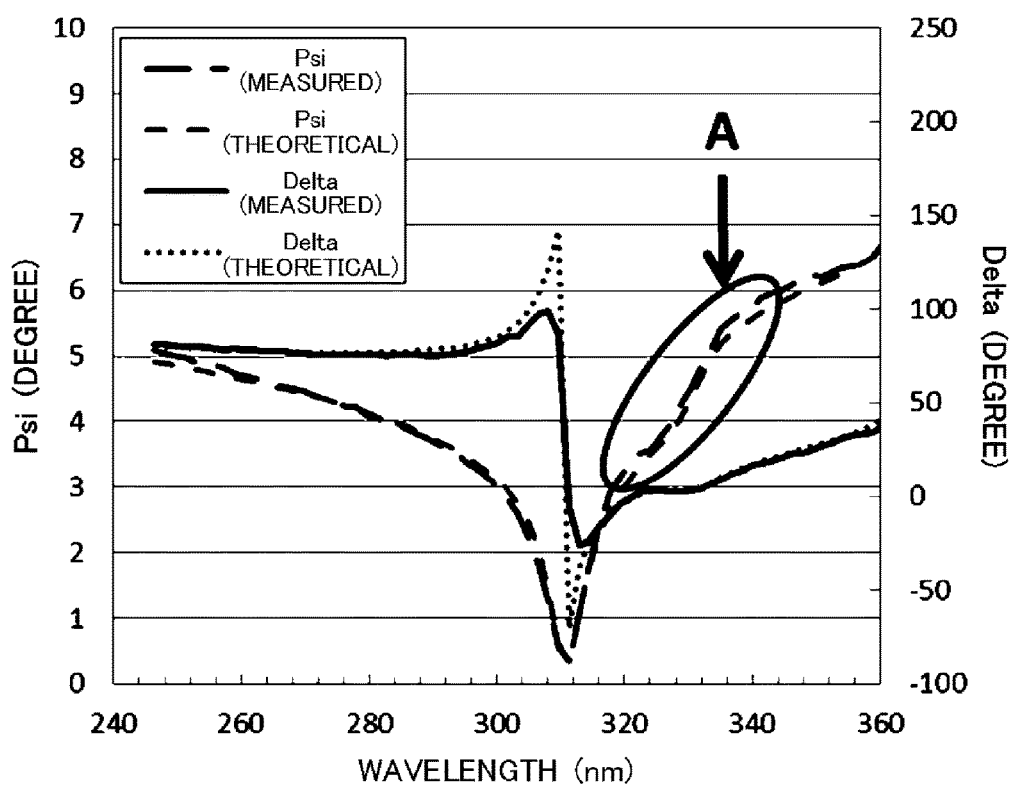
FIG. 26 is a chart showing spectroscopic ellipsometric data measurement values and theoretical values obtained if an absorption model in which light is absorbed in a specific excitation generating wavelength region is applied to a GaN layer.

In view of this, an absorption model in which absorption does not occur in a wavelength region where absorption occurs intrinsically with bulk GaN, and absorption occurs in other wavelength regions (absorption model in which light is absorbed in a specific excitation generating wavelength region) was employed to perform analysis. FIG. 26 is a chart showing spectroscopic ellipsometric data measurement values and theoretical values obtained if an absorption model in which light is absorbed in a specific excitation generating wavelength region is applied to the GaN layer, and it can be known that the values match well even in a part where a kinks occurs indicated with A in the figure.

Example 4

As Example 4, a case where the layer count n of measurement-target monolayers included in the measurement-target layer 106 is two is explained. As a sample substrate for measurement of Example 4, a sample laminate substrate similar to the substrate in Example 3 was prepared. The base substrate 102, the intermediate layer 120, the buffer layer 126, the absorption layer 108, the first measurement-target monolayer 104a and the third measurement-target monolayer 104c are similar to those in Example 3. Note that the GaN layer (the third measurement-target monolayer 104c) in Example 4 was a p-type GaN layer, and has a thickness of 90 nm. Such a GaN layer can be applied as an active layer of a normally-off transistor. Also, the base substrate 102 in Example 4 was an 8 inch-diameter silicon wafer substrate.

Similar to Example 3, in measurement of the sample laminate substrate of Example 4, it was irradiated with the incident light 112, spectroscopic ellipsometric data was acquired from the reflected light 114, and the film thicknesses and compositions of the $Al_{0.25}Ga_{0.75}N$ layer and GaN layer were calculated using the spectroscopic ellipsometric data. The threshold wavelength (λth) used was 370 nm, an analysis model employed in fitting of the GaN layer (the third measurement-target monolayer 104c) was an absorption model.

Figure 27:
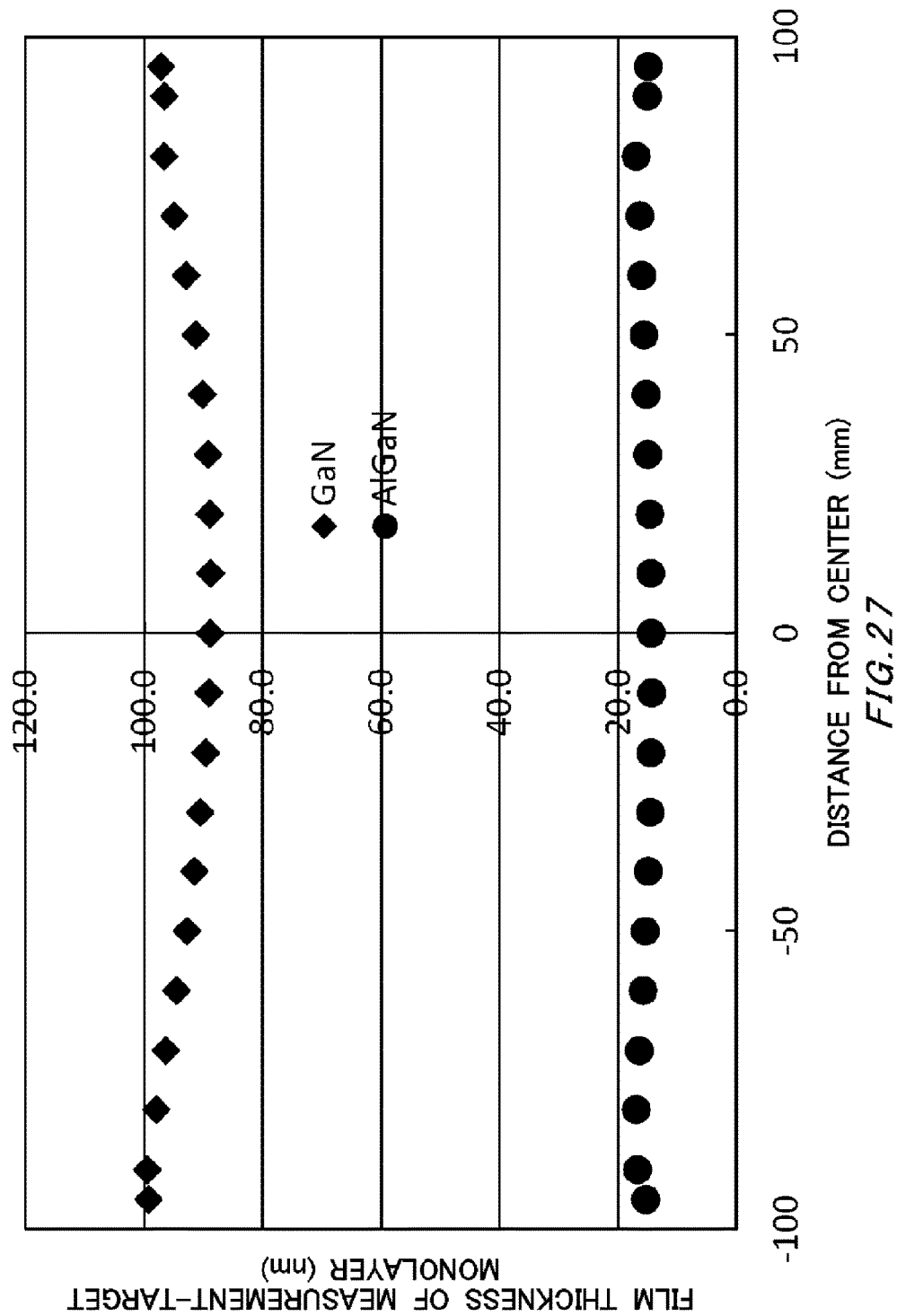
FIG. 27 is a chart obtained by plotting film thicknesses of an $Al_{0.25}Ga_{0.75}N$ layer and GaN layer in relation to their distances from the center of a substrate.

FIG. 27 is a chart obtained by plotting film thicknesses of the $Al_{0.25}Ga_{0.75}N$ layer and GaN layer with the horizontal axis indicting their distances from the center (position). The circle-shaped marks indicate film thicknesses of the $Al_{0.25}Ga_{0.75}N$ layer, and the diamond-shaped marks indicate film thicknesses of the GaN layer. It can be known from the figure that measurement could be performed well even if the thickness of the GaN layer was as large as about 90 nm. Examining it together with the result of Example 3, the GaN layer formed as the third measurement-target monolayer 104c could be measured well at least in the range of 1 to 90 nm. Also, as can be read out from the horizontal axis of the figure, measurement was performed with accuracy in the range of about 200 mm (8 inches).

Example 5

As Example 5, a case where the layer count n of measurement-target monolayers included in the measurement-target layer 106 is two is explained. As a sample substrate for measurement of Example 5, a sample laminate substrate similar to the substrate in Example 3 was prepared. The base substrate 102, the intermediate layer 120, the buffer layer 126, the absorption layer 108 and the first measurement-target monolayer 104a are similar to those in Example 3. Note that a silicon nitride (SixN) layer was formed as the third measurement-target monolayer 104c in Example 5. The thickness of the SixN layer was 5 nm. The SixN layer functions as a cap layer of the first measurement-target monolayer 104a. A 6 inch-diameter silicon wafer substrate was used for the base substrate 102.

Similar to Example 3, in measurement of the sample laminate substrate of Example 5, it was irradiated with the incident light 112, spectroscopic ellipsometric data was acquired from the reflected light 114, and the film thicknesses and compositions of the $Al_{0.25}Ga_{0.75}N$ layer and SixN layer were calculated using the spectroscopic ellipsometric data. The threshold wavelength (λth) used was 370 nm, an analysis model employed in fitting of the SixN layer (the third measurement-target monolayer 104c) was an absorption model.

Figure 28:
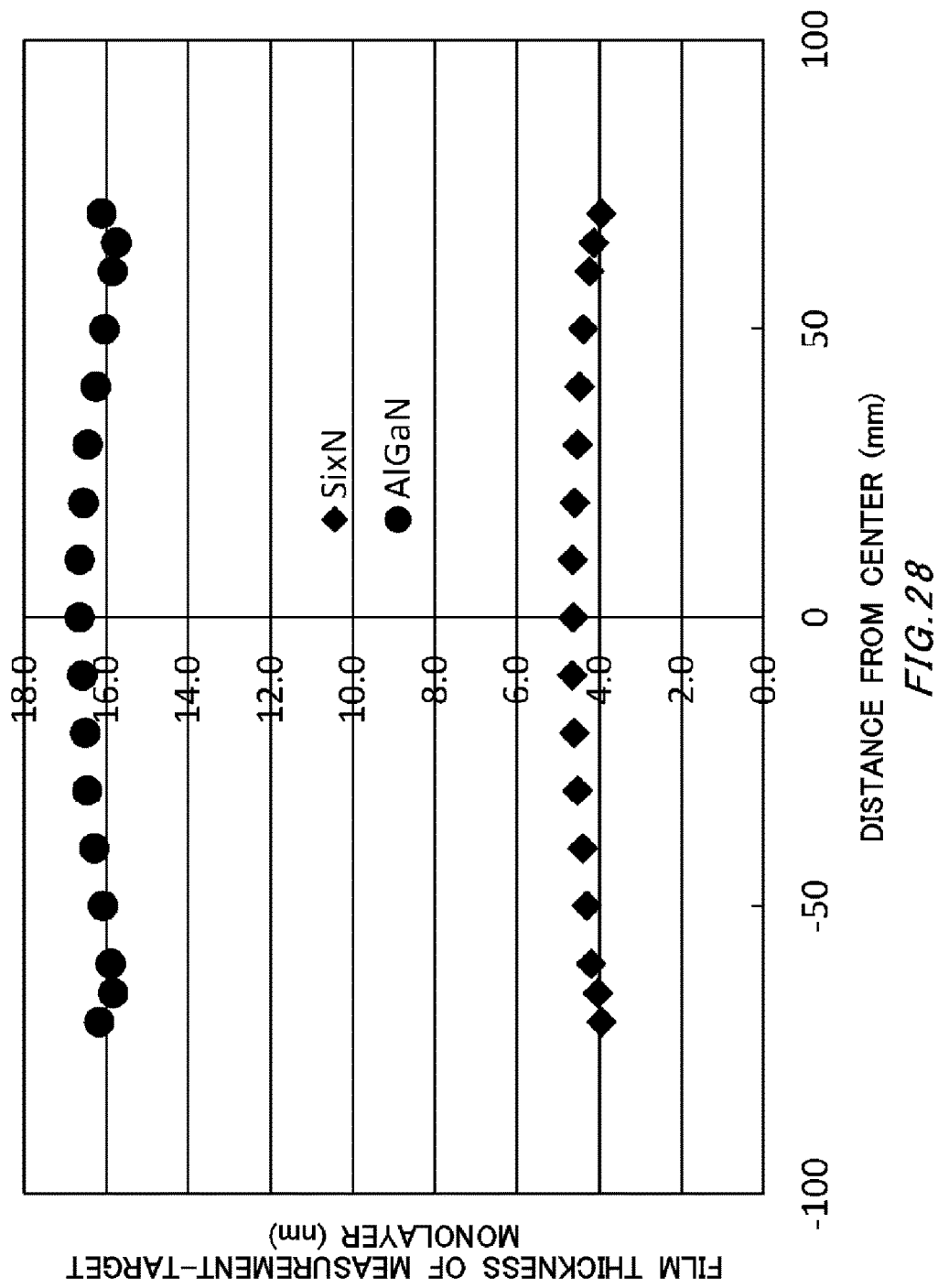
FIG. 28 is a chart obtained by plotting film thicknesses of an $Al_{0.25}Ga_{0.75}N$ layer and SixN layer in relation to their distances from the center of a substrate.

FIG. 28 is a chart obtained by plotting film thicknesses of the $Al_{0.25}Ga_{0.75}N$ layer and SixN layer with the horizontal axis indicting their distances from the center (position). The circle-shaped marks indicate film thicknesses of the $Al_{0.25}Ga_{0.75}N$ layer, and the diamond-shaped marks indicate film thicknesses of the SixN layer. It can be known from the figure that the thickness of the SixN layer which is approximately 5 nm was measured well over the entire region of the 6-inch substrate.

Example 6

As Example 6, a case where the layer count n of measurement-target monolayers included in the measurement-target layer 106 is two is explained. As a sample substrate for measurement of Example 6, a sample laminate substrate similar to the substrate in Example 2 was prepared. The base substrate 102, the intermediate layer 120, the buffer layer 126, the absorption layer 108, the first measurement-target monolayer 104a and the second measurement-target monolayer 104b were similar to those in Example 2. Note that in Example 6, three types of sample laminate substrate were prepared as experiment examples 1 and 2, and a comparative example 1. The design values of compositions and film thicknesses of the AlGaN layer (the first measurement-target monolayer 104a), and the design value of the film thickness of the AlN layer (the second measurement-target monolayer 104b) in the experiment examples 1 and 2 and the comparative example 1 were as shown in Table 1. That is, the respective design values of the composition and film thickness of the AlGaN layer, and the film thickness of the AlN layer in the experiment example 1 were 0.17, 20 nm and 1.00 nm, respectively. The respective design values of the composition and film thickness of the AlGaN layer, and the film thickness of the AlN layer in the experiment example 2 were 0.15, 20 nm and 0.85 nm, respectively. The respective design values of the composition and film thickness of the AlGaN layer, and the film thickness of the AlN layer in the comparative example 1 were 0.26, 20 nm and 1.70 nm, respectively. Also, reference samples having only AlGaN layers as the measurement-target layer 106, not including AlN layers, were prepared for each of the experiment examples 1 and 2, and the comparative example 1. The reference samples were used as samples to be used as initial values of fitting parameters explained later, or for obtaining reference mobility for calculating mobility ratios.

TABLE 1

| | AlGaN layer | | AlN layer | | | |
|---|---|---|---|---|---|---|
| | Al composition | Film thickness (nm) | Film thickness (nm) | Absorption edge energy (eV) | Absorption edge wavelength (nm) | Mobility ratio |
| Experiment Example 1 | 0.17 | 20 | 1.00 | 4.156 | 298.4 | 1.200 |
| Experiment Example 2 | 0.15 | 20 | 0.85 | 3.973 | 312.1 | 1.309 |
| Comparative Example 1 | 0.26 | 20 | 1.70 | 4.423 | 280.4 | 0.995 |

Similar to Example 2, in measurement of the sample laminate substrate of Example 6, it was irradiated with the incident light 112, spectroscopic ellipsometric data was acquired from the reflected light 114, and the film thicknesses and compositions of the AlGaN layer and AlN layer (the respective measurement-target monolayers included in the measurement-target layer 106) were calculated using the spectroscopic ellipsometric data. The threshold wavelength (λth) used was 370 nm. Note that an analysis model applied in fitting of the AlN layer (the second measurement-target monolayer 104b) was an absorption model.

Prior to the measurement of the sample laminate substrates, measurement was performed for the reference sample, the film thicknesses and optical constants of AlGaN layers were obtained in advance, and the film thicknesses and optical constants obtained about the AlGaN layers in the reference samples were used as initial values of parameters in fitting of the sample laminate substrates. Also, in fitting of the sample laminate substrates, values of film thicknesses among parameters about the AlGaN layer and the AlN layer were obtained in preliminary fitting, and the value of film thicknesses obtained in the preliminary fitting were used as initial values of the parameters in fitting of the sample laminate substrates. In this manner, using, as initial values of fitting parameters, values obtained in fitting of the AlGaN layer formed separately as reference samples, film thickness values obtained in preliminary fitting or the like, it is possible to attain convergence to a suitable minimum in fitting, and enhance the precision of fitting results. Also, it is possible to attain convergence faster in calculation of fitting.

Among the value related to the AlN layer obtained by the above-mentioned fitting, values of absorption edges which are one of the parameters in the absorption model are shown in Table 1, for each of the experiment examples 1 and 2 and the comparative example 1. As values of absorption edges, energy values and wavelengths are shown, but both the values are different merely in terms of expression, and have the same physical meanings. Also, for each of the experiment examples 1 and 2, and the comparative example 1, the mobility at a 2DEG channel formed at the interface between the GaN layer (the absorption layer 108) and the AlGaN layer (the first measurement-target monolayer 104a) was measured. For each of the experiment examples 1 and 2, and the comparative example 1, the mobility is normalized using, as a reference, the mobility in the reference samples corresponding to a case where there are no AlN layers, and was evaluated as the mobility ratio. The mobility ratio of each of the experiment example 1 and 2, and the comparative example 1 is shown in Table 1.

Figure 29:
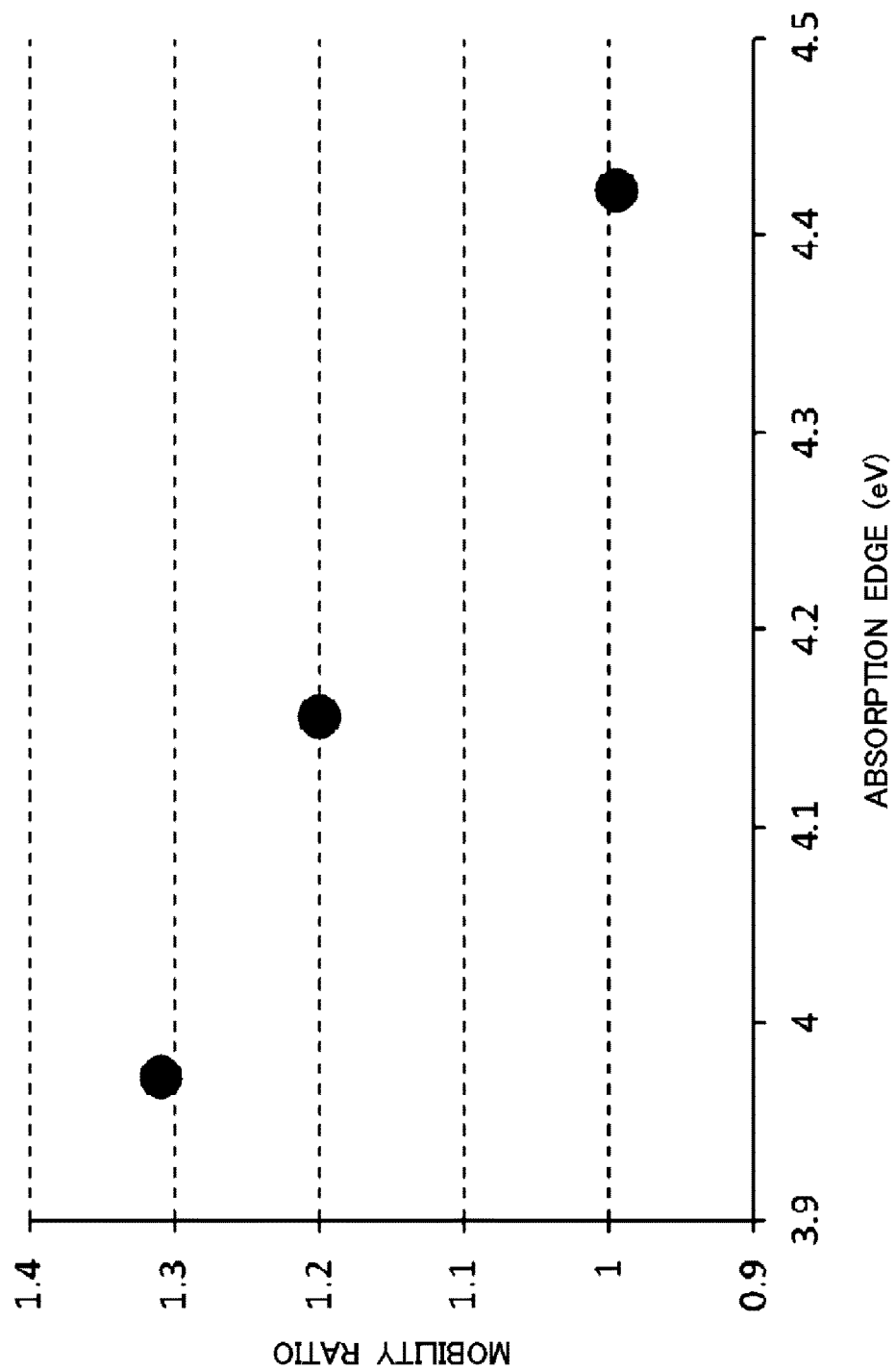
FIG. 29 is a chart obtained by plotting values of the mobility ratio in relation to absorption edge energy values.

FIG. 29 is a chart obtained by plotting values of the mobility ratio shown in Table 1 with the horizontal axis indicating absorption edge energy values. As is obvious from Table 1, in the experiment examples 1 and 2, the mobility is improved (the mobility ratio exceeds 1) by forming the AlN layer (the second measurement-target monolayer 104b) between the GaN layer (the absorption layer 108) and the AlGaN layer (the first measurement-target monolayer 104a), but in the comparative example 1, the mobility lowers (the mobility ratio falls below 1) conversely, by forming the AlN layer. Examining this in FIG. 29, in the AlN layer that indicates the absorption edge energy value exceeding 4.4 eV, the mobility enhancement effect is not observed, or the feature becomes a hindrance to mobility enhancement; on the contrary, in the AlN layer that indicates the absorption edge energy value of 4.4 eV or lower, the mobility enhancement effect can be attained.

In the present embodiments described so far, the invention was explained as a laminate substrate measurement method, but the present invention can also be grasped as a laminate substrate suited to the measurement method. That is, the present invention may be a laminate substrate 110 that is applicable to a laminate substrate measurement method, wherein the laminate substrate measurement method includes: emitting the incident light 112 including light with a wavelength shorter than a threshold wavelength toward a surface on a side on which the measurement-target layer 106 including the measurement-target monolayer 105 or the measurement-target laminate layer 104 formed by laminating a plurality of the measurement-target monolayers is positioned, and measuring the reflected light 114 of the incident light 112 and acquiring mutually independent two or more reflected light-related values for wavelengths equal to the threshold wavelength or shorter; and calculating values related to the measurement-target monolayers for each measurement-target monolayer included in the measurement-target layer 106 using 2n (n is a layer count of the measurement-target monolayers included in the measurement-target layer 106 and is an integer equal to one or larger) or more reflected light-related values, the laminate substrate 110 includes the base substrate 102; the measurement-target layer 106; and the absorption layer 108 positioned between the base substrate 102 and the measurement-target layer 106, and the threshold wavelength used in the measurement method is the maximum wavelength in a wavelength range over which the absolute value of a first-order derivative $dk(\lambda)/d\lambda$ obtained if the extinction coefficient k of the absorption layer is expressed as the function $k(\lambda)$ of the wavelength λ (expressed in nm) becomes equal to an extinction derivative threshold value or lower. The extinction derivative threshold value refers to a value defined to indicate where the extinction coefficient changes rapidly. The extinction derivative threshold value is preferably $1\times10^{-3}$, more preferably $5\times10^{-4}$, and further preferably $1\times10^{-4}$.

The fact that each measurement-target monolayer included in the measurement-target layer 106 and the absorption layer 108 may consist of semiconductors or dielectrics having mutually different compositions; the configurations of the measurement-target layer 106 and the absorption layer 108; specific specifications about substances and thicknesses; or the like are as described in the above-mentioned embodiments.

Also, the present invention can be grasped as a laminate substrate such that if the layer count n of the measurement-target monolayers included in the measurement-target layer 106 is two or more, the measurement-target layer 106 includes the first measurement-target monolayer 104a and the second measurement-target monolayer 104b, the second measurement-target monolayer 104b is positioned closer to the absorption layer 108 than the first measurement-target monolayer 104a is, and a value related to the second measurement-target monolayer 104b is calculated by curve fitting based on an absorption model in which light is absorbed by the second measurement-target monolayer 104b in a specific excitation generating wavelength region, an energy value at an absorption edge in the absorption model obtained as one of values related to the second measurement-target monolayer 104b by the curve fitting is 4.4 eV or lower, and further preferably 4.2 eV or lower. Furthermore, the present invention can be grasped as the laminate substrate in which the base substrate 102 is a wafer substrate having a diameter of 150 mm or larger.

Also, the present invention can be grasped as a measurement apparatus applicable to the measurement method. That is, the present invention can be grasped as a measurement apparatus that is applicable to the measurement method described in the above-mentioned embodiment, and includes a substrate holding unit that holds the laminate substrate 110; a light source unit that generates the incident light 112; a reception-light signal generating unit that receives the reflected light 114 and generates a reception-light signal; an angle control mechanism that controls angles of the substrate holding unit, the light source unit and the reception-light signal generating unit; and a signal processing unit that processes the reception-light signal generated at the reception-light signal generating unit.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. A laminate substrate measurement method for a laminate substrate having: a base substrate; a measurement-target layer; and an absorption layer positioned between the base substrate and the measurement-target layer, wherein
   the measurement-target layer includes: a measurement-target monolayer which is a monolayer or a measurement-target laminate layer formed by laminating a plurality of the measurement-target monolayers,
   the laminate substrate measurement method comprises:
      emitting incident light including light with a wavelength shorter than a threshold wavelength toward a surface of the laminate substrate on a side on which the measurement-target layer is positioned, and measuring reflected light of the incident light from the laminate substrate and acquiring mutually independent 2n (n is a layer count of the measurement-target monolayers included in the measurement-target layer and is an integer equal to one or larger) or more reflected light-related values for wavelengths equal to the threshold wavelength or shorter; and
      calculating values related to the measurement-target monolayers for each measurement-target monolayer included in the measurement-target layer using the 2n or more reflected light-related values, and
   the threshold wavelength used is a maximum wavelength in a wavelength range over which an absolute value of a first-order derivative $dk(\lambda)/d\lambda$ obtained if an extinction coefficient k of the absorption layer is expressed as a function $k(\lambda)$ of a wavelength $\lambda$ (expressed in nm) becomes equal to an extinction derivative threshold value or lower.

2. The measurement method according to claim 1, wherein in the acquiring, an angle of incidence of the incident light is fixed, and as the reflected light-related values, one or more values selected from two polarized components and reflectance of the reflected light are acquired for 2n or more wavelengths.

3. The measurement method according to claim 2, wherein spectrometry is performed on the reflected light, and as the reflected light-related values, one or more spectral values selected from two spectral polarized components and spectral reflectance of the reflected light are acquired.

4. The measurement method according to claim 3, wherein the incident light used is linearly polarized light, and spectroscopic phase difference ($\Delta$) and spectral reflection amplitude ratio angle (tan $\Psi$) of s-polarized light and p-polarized light are acquired as two spectral polarized components of the reflected light.

5. The measurement method according to claim 1, wherein in the acquiring, an angle of incidence of the incident light is fixed, and as the reflected light-related values, two or more values selected from two polarized components and reflectance of the reflected light are acquired for n or more wavelengths.

6. The measurement method according to claim 1, wherein
   a layer count n of the measurement-target monolayers included in the measurement-target layer is two or more, and
   in the acquiring, the reflected light is measured for n or more angles of incidence of the incident light, and as the reflected light-related values, two or more values selected from two polarized components and reflectance of the reflected light are acquired for each of the angles of incidence.

7. The measurement method according to claim 1, wherein in the acquiring, the reflected light is measured for 2n or more angles of incidence of the incident light, and as the reflected light-related values, one or more values selected from two polarized components and reflectance of the reflected light are acquired for each of the angles of incidence.

8. The measurement method according to claim 1, wherein in the calculating, for each measurement-target monolayer included in the measurement-target layer, a thickness of the measurement-target monolayer and a value related to the measurement-target monolayer are calculated by curve fitting based on an analysis model.

9. The measurement method according to claim 8, wherein
a layer count n of the measurement-target monolayers included in the measurement-target layer is two or more, and
the analysis model employed is an absorption model in which one or more of the measurement-target monolayers among two or more of the measurement-target monolayers absorb light in a specific excitation generating wavelength region.

10. The measurement method according to claim 8, wherein the analysis model is a dielectric function model that satisfies a Kramers-Kronig relation.

11. The measurement method according to claim 10, wherein the dielectric function model includes a parametric semiconductor model or a Tauc-Lorenz model.

12. The measurement method according to claim 8, wherein
a layer count n of the measurement-target monolayers included in the measurement-target layer is two or more, and
the analysis model employed is a transmission model in which one or more of the measurement-target monolayers among two or more of the measurement-target monolayers entirely transmit light in a measured wavelength region.

13. The measurement method according to claim 1, wherein each measurement-target monolayer included in the measurement-target layer and the absorption layer consist of semiconductors or dielectrics having mutually different compositions.

14. The measurement method according to claim 13, wherein
a layer count n of the measurement-target monolayers included in the measurement-target layer is two or more,
the measurement-target layer includes a first measurement-target monolayer and a second measurement-target monolayer, and the second measurement-target monolayer is positioned closer to the absorption layer than the first measurement-target monolayer is,
the first measurement-target monolayer consists of $In_{x1}Al_{x2}Ga_{x3}N$ (x1+x2+x3=1),
the second measurement-target monolayer consists of $In_{z1}Al_{z2}Ga_{z3}N$ (z1+z2+z3=1), and
the second measurement-target monolayer has a bandgap larger than a bandgap of the first measurement-target monolayer.

15. The measurement method according to claim 14, wherein
the first measurement-target monolayer consists of $Al_{x2}Ga_{x3}N$ (x2+x3=1, 0<x2≤0.5), and
the second measurement-target monolayer consists of AlN.

16. The measurement method according to claim 14, wherein
in the calculating, for each measurement-target monolayer included in the measurement-target layer, a thickness of the measurement-target monolayer and a value related to the measurement-target monolayer are calculated by curve fitting based on an analysis model,
the analysis model of the curve fitting in the calculating employed for the second measurement-target monolayer is an absorption model in which light is absorbed in a specific excitation generating wavelength region, and
in the curve fitting in the calculating, a value related to a monolayer that is manufactured under the same condition as the first measurement-target monolayer is set to an initial value of a parameter related to the first measurement-target monolayer, the value being determined in advance in preliminary measurement targeted at the monolayer.

17. The measurement method according to claim 14, wherein
in the calculating, for each measurement-target monolayer included in the measurement-target layer, a thickness of the measurement-target monolayer and a value related to the measurement-target monolayer are calculated by curve fitting based on an analysis model,
the analysis model of the curve fitting in the calculating employed for the second measurement-target monolayer is an absorption model in which light is absorbed in a specific excitation generating wavelength region, and
in the curve fitting in the calculating, thicknesses of the first measurement-target monolayer and the second measurement-target monolayer obtained by preliminary curve fitting targeted at the first measurement-target monolayer and the second measurement-target monolayer are set to initial values of parameters related to the first measurement-target monolayer and the second measurement-target monolayer.

18. The measurement method according to claim 14, wherein in the calculating, for each measurement-target monolayer included in the measurement-target layer, a thickness and mixed crystal ratio of the measurement-target monolayer are calculated by curve fitting based on an analysis model.

19. The measurement method according to claim 14, wherein
the absorption layer consists of $In_{y1}Al_{y2}Ga_{y3}N$ (y1+y2+y3=1), and
the absorption layer has a bandgap smaller than a bandgap of the first measurement-target monolayer.

20. The measurement method according to claim 19, wherein
the absorption layer consists of GaN, and
the threshold wavelength is 370 nm.

21. The measurement method according to claim 13, wherein
a layer count n of the measurement-target monolayers included in the measurement-target layer is two or more,
the measurement-target layer includes a first measurement-target monolayer and a third measurement-target monolayer, and the first measurement-target monolayer is positioned closer to the absorption layer than the third measurement-target monolayer is,
the first measurement-target monolayer consists of $In_{x1}Al_{x2}Ga_{x3}N$ (x1+x2+x3=1), the third measurement-target monolayer consists of $In_{q1}Al_{q2}Ga_{q3}N$ (q1+q2+q3=1), and
the third measurement-target monolayer has a bandgap smaller than a bandgap of the first measurement-target monolayer.

22. The measurement method according to claim 21, wherein
the first measurement-target monolayer consists of $Al_{x2}Ga_{x3}N$ (x2+x3=1, 0<x2≤0.5), and
the third measurement-target monolayer consists of GaN.

23. The measurement method according to claim 22, wherein
the third measurement-target monolayer consists of p-type GaN, and
a thickness of the third measurement-target monolayer is larger than a thickness of the first measurement-target monolayer.

24. The measurement method according to claim 13, wherein
a layer count n of the measurement-target monolayers included in the measurement-target layer is two or more,
the measurement-target layer includes a first measurement-target monolayer and a third measurement-target monolayer, and the first measurement-target monolayer is positioned closer to the absorption layer than the third measurement-target monolayer is,
the first measurement-target monolayer consists of $In_{x1}Al_{x2}Ga_{x3}N$ (x1+x2+x3=1), and
the third measurement-target monolayer consists of silicon nitride.

25. The measurement method according to claim 13, wherein
a layer count n of the measurement-target monolayer included in the measurement-target layer is 1, and
the measurement-target monolayer consists of $In_{x1}Al_{x2}Ga_{x3}N$ (x1+x2+x3=1).

26. The measurement method according to claim 25, wherein the measurement-target monolayer consists of $Al_{x2}Ga_{x3}N$ (x2+x3=1, 0<x2≤0.5).

27. The measurement method according to claim 25, wherein in the calculating, a thickness and mixed crystal ratio (values of x1, x2 and x3) of the measurement-target monolayer are calculated by curve fitting based on an analysis model.

28. The measurement method according to claim 25, wherein
the absorption layer consists of $In_{y1}Al_{y2}Ga_{y3}N$ (y1+y2+y3=1), and
the absorption layer has a bandgap smaller than a bandgap of the measurement-target monolayer.

29. The measurement method according to claim 1, wherein a thickness of the absorption layer is equal to or larger than a light penetrating depth at a wavelength at which a second-order derivative $d2k(\lambda)/d\lambda 2$ becomes zero if an extinction coefficient k of the absorption layer is expressed as a function $k(\lambda)$ of a wavelength λ (expressed in nm).

30. The measurement method according to claim 29, wherein
the absorption layer consists of GaN, and
a thickness of the absorption layer that consists of GaN is 240 nm or larger.

31. A measurement apparatus that is applicable to the measurement method according to claim 1, the measurement apparatus comprising:
a substrate holding unit that holds the laminate substrate;
a light source unit that generates the incident light;
a reception-light signal generating unit that receives the reflected light and generates a reception-light signal;
an angle control mechanism that controls angles of the substrate holding unit, the light source unit and the reception-light signal generating unit; and
a signal processing unit that processes the reception-light signal generated at the reception-light signal generating unit.

32. A laminate substrate that is applicable to a laminate substrate measurement method, wherein
the laminate substrate measurement method includes:
emitting incident light including light with a wavelength shorter than a threshold wavelength toward a surface on a side on which a measurement-target layer including a measurement-target monolayer or a measurement-target laminate layer formed by laminating a plurality of the measurement-target monolayers is positioned, and measuring reflected light of the incident light and acquiring mutually independent two or more reflected light-related values for wavelengths equal to the threshold wavelength or shorter; and
calculating values related to the measurement-target monolayers for each measurement-target monolayer included in the measurement-target layer using 2n (n is a layer count of the measurement-target monolayers included in the measurement-target layer and is an integer equal to one or larger) or more reflected light-related values,
the laminate substrate comprises a base substrate; the measurement-target layer; and an absorption layer positioned between the base substrate and the measurement-target layer, and
the threshold wavelength used in the measurement method is a maximum wavelength in a wavelength range over which an absolute value of a first-order derivative $dk(\lambda)/d\lambda$ obtained if an extinction coefficient k of the absorption layer is expressed as a function $k(\lambda)$ of a wavelength λ (expressed in nm) becomes equal to an extinction derivative threshold value or lower.

33. The laminate substrate according to claim 32, wherein each measurement-target monolayer included in the measurement-target layer and the absorption layer consist of semiconductors or dielectrics having mutually different compositions.

34. The laminate substrate according to claim 33, wherein
a layer count n of the measurement-target monolayers included in the measurement-target layer is two or more,
the measurement-target layer includes a first measurement-target monolayer and a second measurement-target monolayer, and the second measurement-target monolayer is positioned closer to the absorption layer than the first measurement-target monolayer is,
the first measurement-target monolayer consists of $In_{x1}Al_{x2}Ga_{x3}N$ (x1+x2+x3=1),
the second measurement-target monolayer consists of $In_{z1}Al_{z2}Ga_{z3}N$ (z1+z2+z3=1), and
the second measurement-target monolayer has a bandgap larger than a bandgap of the first measurement-target monolayer.

35. The laminate substrate according to claim 34, wherein
the first measurement-target monolayer consists of $Al_{x2}Ga_{x3}N$ (x2+x3=1, 0<x2≤0.5), and
the second measurement-target monolayer consists of AlN.

36. The laminate substrate according to claim 34, wherein
the absorption layer consists of $In_{y1}Al_{y2}Ga_{y3}N$ (y1+y2+y3=1), and
the absorption layer has a bandgap smaller than a bandgap of the first measurement-target monolayer.

37. The laminate substrate according to claim 36, wherein
the absorption layer consists of GaN, and
the threshold wavelength is 370 nm.

38. The laminate substrate according to claim 33, wherein
a layer count n of the measurement-target monolayers included in the measurement-target layer is two or more,
the measurement-target layer includes a first measurement-target monolayer and a third measurement-target monolayer, and the first measurement-target monolayer is positioned closer to the absorption layer than the third measurement-target monolayer is,
the first measurement-target monolayer consists of $In_{x1}Al_{x2}Ga_{x3}N$ (x1+x2+x3=1),
the third measurement-target monolayer consists of $In_{q1}Al_{q2}Ga_{q3}N$ (q1+q2+q3=1), and
the third measurement-target monolayer has a bandgap smaller than a bandgap of the first measurement-target monolayer.

39. The laminate substrate according to claim 38, wherein
the first measurement-target monolayer consists of $Al_{x2}Ga_{x3}N$ (x2+x3=1, 0<x2≤0.5), and
the third measurement-target monolayer consists of GaN.

40. The laminate substrate according to claim 38, wherein
the third measurement-target monolayer consists of p-type GaN, and
a thickness of the third measurement-target monolayer is larger than a thickness of the first measurement-target monolayer.

41. The laminate substrate according to claim 33, wherein
a layer count n of the measurement-target monolayers included in the measurement-target layer is two or more,
the measurement-target layer includes a first measurement-target monolayer and a third measurement-target monolayer, and the first measurement-target monolayer is positioned closer to the absorption layer than the third measurement-target monolayer is,
the first measurement-target monolayer consists of $In_{x1}Al_{x2}Ga_{x3}N$ (x1+x2+x3=1), and
the third measurement-target monolayer consists of silicon nitride.

42. The laminate substrate according to claim 33, wherein
a layer count n of the measurement-target monolayer included in the measurement-target layer is 1, and
the measurement-target monolayer consists of $In_{x1}Al_{x2}Ga_{x3}N$ (x1+x2+x3=1).

43. The laminate substrate according to claim 42, wherein
the measurement-target monolayer consists of $Al_{x2}Ga_{x3}N$ (x2+x3=1, 0<x2≤0.5).

44. The laminate substrate according to claim 42, wherein
the absorption layer consists of $In_{y1}Al_{y2}Ga_{y3}N$ (y1+y2+y3=1), and
the absorption layer has a bandgap smaller than a bandgap of the measurement-target monolayer.

45. The laminate substrate according to claim 32, wherein
a thickness of the absorption layer is equal to or larger than a light penetrating depth at a wavelength at which a second-order derivative $d2k(\lambda)/d\lambda 2$ becomes 0 if an extinction coefficient k of the absorption layer is expressed as a function $k(\lambda)$ of a wavelength $\lambda$ (expressed in nm).

46. The laminate substrate according to claim 45, wherein
the absorption layer consists of GaN, and
a thickness of the absorption layer that consists of GaN is 240 nm or larger.

47. The laminate substrate according to claim 32, wherein
a layer count n of the measurement-target monolayers included in the measurement-target layer is two or more,
the measurement-target layer includes a first measurement-target monolayer and a second measurement-target monolayer, and the second measurement-target monolayer is positioned closer to the absorption layer than the first measurement-target monolayer is,
the second measurement-target monolayer is a monolayer for which a value related to the second measurement-target monolayer is calculated by curve fitting based on an absorption model in which light is absorbed in a specific excitation generating wavelength region, and
an energy value at an absorption edge in the absorption model obtained as one of values related to the second measurement-target monolayer by the curve fitting is 4.4 eV or lower.

48. The laminate substrate according to claim 32, wherein
the base substrate is a wafer substrate having a diameter of 150 mm or larger.

* * * * *